United States Patent
Levitzki et al.

(10) Patent No.: US 10,543,232 B2
(45) Date of Patent: *Jan. 28, 2020

(54) POLYPLEX OF DOUBLE-STRANDED RNA AND POLYMERIC CONJUGATE

(71) Applicant: TARGIMMUNE THERAPEUTICS AG, Basel (CH)

(72) Inventors: Alex Levitzki, Jerusalem (IL); Salim Joubran, Lod (IL); Alexei Shir, Jerusalem (IL); Maya Zigler, Neve Ilan (IL); Alaa Talhami, Maghar Village (IL); Yael Langut, Haifa (IL)

(73) Assignee: TargImmune Therapeutics AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,133

(22) Filed: Mar. 8, 2019

(65) Prior Publication Data

US 2019/0192563 A1 Jun. 27, 2019

Related U.S. Application Data

(63) Continuation of application No. 15/310,735, filed as application No. PCT/IL2015/050514 on May 14, 2015, now Pat. No. 10,278,991.

(60) Provisional application No. 61/993,110, filed on May 14, 2014.

(51) Int. Cl.
| | |
|---|---|
| A61K 47/34 | (2017.01) |
| A61K 35/14 | (2015.01) |
| A61K 45/06 | (2006.01) |
| C12N 15/117 | (2010.01) |
| A61K 47/60 | (2017.01) |
| A61K 47/59 | (2017.01) |
| A61K 35/17 | (2015.01) |

(52) U.S. Cl.
CPC .............. *A61K 35/14* (2013.01); *A61K 45/06* (2013.01); *A61K 47/59* (2017.08); *A61K 47/60* (2017.08); *C12N 15/117* (2013.01); *A61K 35/17* (2013.01); *C12N 2310/17* (2013.01); *C12N 2310/351* (2013.01); *C12N 2310/53* (2013.01)

(58) Field of Classification Search
CPC ........ A61K 35/14; A61K 35/17; A61K 45/06; A61K 47/59; A61K 47/60; A61K 47/48192; C12N 15/117; C12N 2310/17; C12N 2310/351; C12N 2310/53
USPC ...... 424/193.1, 277.1, 278.1, 280.1; 435/455
See application file for complete search history.

(56) References Cited

U.S. PATENT DOCUMENTS

| | | | |
|---|---|---|---|
| 7,893,244 B2 | 2/2011 | Liu et al. | |
| 8,461,224 B2 | 6/2013 | Lin et al. | |
| 8,969,543 B2 | 3/2015 | Jeong et al. | |
| 9,006,406 B2 | 4/2015 | Levitzki et al. | |
| 10,278,991 B2 * | 5/2019 | Levitzki | A61K 45/06 |
| 2004/0043030 A1 | 3/2004 | Griffiths et al. | |
| 2004/0247680 A1 | 12/2004 | Farokhzad et al. | |
| 2005/0118718 A1 | 6/2005 | Bae et al. | |
| 2006/0110746 A1 | 5/2006 | Andre et al. | |
| 2007/0225213 A1 | 9/2007 | Kosak | |
| 2010/0266642 A1 | 10/2010 | Langer et al. | |
| 2010/0278927 A1 | 11/2010 | Mirosevich et al. | |
| 2011/0256227 A1 | 10/2011 | Mirosevich et al. | |
| 2012/0021006 A1 | 1/2012 | Levitzki et al. | |
| 2012/0207795 A1 | 8/2012 | Zink et al. | |
| 2015/0258102 A1 | 9/2015 | Bagrodia et al. | |

FOREIGN PATENT DOCUMENTS

| | | |
|---|---|---|
| CA | 2872304 A1 | 11/2013 |
| CN | 101638484 A | 2/2010 |
| CN | 104341488 A | 2/2015 |
| EP | 2113257 A1 | 11/2009 |
| EP | 2123304 A1 | 11/2009 |
| EP | 2395041 A1 | 12/2011 |
| FR | 2963350 | 2/2012 |
| JP | 2012513210 A | 6/2012 |
| WO | WO 9117773 A2 | 11/1991 |
| WO | WO 9213570 A2 | 8/1992 |
| WO | WO 9307282 A1 | 4/1993 |
| WO | WO 9307283 A1 | 4/1993 |
| WO | WO 9859064 A1 | 12/1998 |
| WO | WO 2004/013310 A2 | 8/2002 |
| WO | WO 02065963 A1 | 8/2002 |
| WO | WO 03045436 A1 | 6/2003 |
| WO | WO 03046185 A1 | 9/2003 |
| WO | WO 03072636 A1 | 9/2003 |
| WO | WO 2004/045491 A2 | 6/2004 |

(Continued)

OTHER PUBLICATIONS https://www.creativepegworks.com/heterobifunctional%20PEG.html (2013). (Year: 2013).

(Continued)

*Primary Examiner* — Janet L Epps-Smith
(74) *Attorney, Agent, or Firm* — Knobbe, Martens, Olson & Bear, LLP

(57) ABSTRACT

A polyplex of a double stranded RNA (dsRNA) and a polymeric conjugate consists of a linear polyethyleneimine (PEI) covalently linked to one or more polyethylene glycol (PEG) moieties. Each PEG moiety is conjugated via a linker to a targeting moiety capable of binding to a cancer antigen. Exemplary cancer antigens include epidermal growth factor receptor (EGFR), human epidermal growth factor receptor 2 (HER2) and prostate surface membrane antigen (PSMA).

23 Claims, 13 Drawing Sheets
Specification includes a Sequence Listing.

(56) References Cited

FOREIGN PATENT DOCUMENTS

| | | |
|---|---|---|
| WO | WO 2004/087931 A1 | 10/2004 |
| WO | WO 2005/090570 A1 | 9/2005 |
| WO | WO 2007/084797 A1 | 7/2007 |
| WO | WO 2007/133812 A2 | 11/2007 |
| WO | WO 2009/110939 A2 | 12/2007 |
| WO | WO 2008/105773 A2 | 9/2008 |
| WO | WO 2008/121949 A1 | 10/2008 |
| WO | WO 2008/124634 A1 | 10/2008 |
| WO | WO 2009/026177 A1 | 2/2009 |
| WO | WO 2009/051837 A2 | 4/2009 |
| WO | WO 2009/131435 A1 | 10/2009 |
| WO | WO 2009/151539 A1 | 12/2009 |
| WO | WO 2010/005740 A2 | 1/2010 |
| WO | WO 2010/073247 | 7/2010 |
| WO | WO 2010/088927 A1 | 8/2010 |
| WO | WO 2011/072114 A1 | 6/2011 |
| WO | WO 2011/084513 A2 | 7/2011 |
| WO | WO 2011/084518 A2 | 7/2011 |
| WO | WO 2011/104169 A1 | 9/2011 |
| WO | WO 2011/108930 A1 | 9/2011 |
| WO | WO 2011/154331 A1 | 12/2011 |
| WO | WO 2012/0005572 A1 | 1/2012 |
| WO | WO 2012/016188 A2 | 2/2012 |
| WO | WO 2012/135592 A2 | 10/2012 |
| WO | WO 2014/078484 A1 | 11/2012 |
| WO | WO 2012/166923 A2 | 12/2012 |
| WO | WO 2014/011053 A1 | 1/2014 |
| WO | WO 2014/062228 A1 | 4/2014 |
| WO | WO 2014/072357 A1 | 5/2014 |
| WO | WO 2014/207231 A1 | 12/2014 |
| WO | WO 2016/123675 A1 | 2/2015 |
| WO | WO 2015/065773 A1 | 5/2015 |
| WO | WO 2015/070080 A2 | 5/2015 |
| WO | WO 2015/144736 A1 | 10/2015 |
| WO | WO 2015/168379 A2 | 11/2015 |
| WO | WO 2017/085228 A1 | 5/2017 |

OTHER PUBLICATIONS

International Search Report issued in application No. PCT/IL2015/050514 dated Aug. 31, 2015.
Supplementary European Search Report received in European Patent Application No. EP 15 79 3532, dated Nov. 28, 2017.
Abourbeh, Galith et al., "PolyIC GE11 Polyplex Inhibits EGFR-Overexpressing Tumors," Apr. 2012. IUBMB Life. (vol. 64, No. 4); pp. 324-330.
Butowski N. et al.: "A phase II clinical trial of poly-ICLC with radiation for adult patients with newly diagnosed 4 supratentorial glioblastoma: a North American Brain Tumor Consortium (NABTC01-05)", Journal of Neuro-Oncology, 91, pp. 175-182, 2009.
Ciceri F. et al: "Antitumor effects of HSV-TK-engineered donor lymphocytes after allogeneic stem-cell transplantation", Blood, vol. 109(11), pp. 4698-4707, Jun. 1, 2007, DOI: 10.1182/3L000-2006-05-023416.
Friedrich I. et al: "RNA Molecules as Anti-Cancer Agents", Seminars in Cancer Biology, vol. 14(4), pp. 223-230, Aug. 1, 2004, DOI: 10.1016/J.SEMCANCER.2004.04.001.
Fujimura T. et al.: "Inhibitory effect of the polyinosinic-polycytidylic acid/cationic liposome on the progression of murine B16F10 melanoma", European Journal of Immunology, vol. 36, pp. 3371-3380, 2006.
Hynes NE. et al.: "ErbB receptors and signaling pathways in cancer" Current Opinion in Cell Biology, vol. 21(2), pp. 177-184, 2009.
Joubran et al., "Optimization of Liganded Polyethylenimine Polyethylene Glycol Vector for Nucleic Acid Delivery", Bioconjugate Chemistry, 25(9):1644-1654 (Aug. 14, 2014).
Li Z.: "Identification and characterization of a novel peptide ligand of epidermal growth factor receptor for targeted delivery of therapeutics" The FASEB Journal, vol. 19, pp. 1978-1985, 2005.
Ogris et al.: "Tumor-targeted gene therapy: strategies for the preparation of ligand-polyethylene glycolpolyethylenimine/DNA complexe", J Controlled Release, vol. 91, pp. 173-181, 2003.
Salazar AM. et al: "Long-term treatment of malignant gliomas with intramuscularly administered polyinosinicpolycytidylic acid stabilized with polylysine and carboxymethylcellulose: an open pilot study", Neurosurgery, vol. 38, pp. 1096-1103, 1996.
Schaffert et al., "Poly (I: C)-mediated tumor growth suppression in EGF-receptor overexpressing tumors using EGF-polyethylene glycol-linear polyethylenimine as carrier", Pharmaceutical Research, 28(4):731-741 (Aug. 6, 2010).
Schafer et al., "Disconnecting the yin and yang relation of epidermal growth factor receptor (EGFR)-mediated delivery: a fully synthetic, EGFR-targeted gene transfer system avoiding receptor activation", Human Gene Therapy, 22(12):1463-1473 (Dec. 31, 2011).
Shir, Alex et al.,"EGF Receptor-Targeted Synthetic Double-Stranded RNA Eliminates Glioblastoma, Breast, Cancer, and Adenocarcinoma Tumors in Mice," PLOS Medicine. Jan. 2006. (vol. 3, Issue 1) pp. 125-135.
Song S. et al.: "Peptide ligand-mediated liposome distribution and targeting to EGFR expressing tumor in vivo", International Journal of Pharmaceutics, vol. 363, pp. 155-161, 2008.
Steven A. Rosenberg: "Overcoming obstacles to the effective immunotherapy of human cancer", PNAS, vol. 105(35), pp. 12643-12644, 2008.
Wolshek et al.: "Specific Systemic Nonviral Gene Delivery to Human Hepatocellular Carcinoma Xenografts in SCID Mice", Hepatology, vol. 36, No. 5, pp. 1106-1104, 2002.
Cardoso A et al., Targeted Lipoplexes for siRNA Delivery. Methods in Enzymology, 465 (2009) 267-287.
Cheol Am Hong and Yoon Sung Nam. Functional Nanostructures for Effective Delivery of Small Interfering RNA Therapeutics. Theranostics. 2014; 4(12): 1211-1232.
Dohmen et al., Nanosized Multifunctional Polyplexes for Receptor-Mediated SiRNA Delivery. ACS Nano. Jun. 26, 2012;6(6): 5198-208.
Edinger et al., 2013, Chimeric Proteins for Targeting EGFR Overexpressing Cancers, Poster abstract, 5th Annual Meeting Israel Society for Cancer Research, May 23, 2013.
Höbel et al., Targeted CRM197-PEG-PEI/siRNA Complexes for Therapeutic RNAi in Glioblastoma. Pharmaceuticals (Basel). Dec. 2011; 4(12): 1591-1606.
Howard et al., Formulation of a microparticle carrier for oral polyplex-based DNA vaccines,Biochimica et Biophysica Acta (BBA), vol. 1674, Issue 2, 2004, pp. 149-157.
Joh et al., Physiological concentrations of human epidermal growth factor in biological fluids: use of a sensitive enzyme immunoassay, Clinica Chimica Acta, 158 (1986) 81-90.
Kawamoto et al., Quantitative Assay of Epidermal Growth Factor Receptor in Human Squamous Cell Carcinomas of the Oral Region by an Avidin-Biotin Method, Jpn. J. Cancer Res. 82, 403-410, Apr. 1991.
Kim S et al., Comparative Evaluation of Target-Specific GFP Gene Silencing Efficiencies for Antisense ODN, Synthetic siRNA, and siRNA Plasmid Complexed with PEI-PEG-FOL Conjugate. Bioconjugate Chem. 2006, 17, 241-244.
Kloeckner J, Prasmickaite L, Høgset A, Berg K, Wagner E. Photochemically enhanced gene delivery of EGF receptor-targeted DNA polyplexes. J Drug Target. May 2004;12(4):205-13.
Kos P et al., Histidine-rich stabilized polyplexes for cMet-directed tumor-targeted gene transfer. Nanoscale, 2015, 7, 5350.
Kullberg E et al., Development of EGF-Conjugated Liposomes for Targeted Delivery of Boronated DNA-Binding Agents. Bioconjugate Chem. 2002, 13, 737-743.
Läychelt U and Wagner E., Nucleic Acid Therapeutics Using Polyplexes: A Journey of 50 Years (and Beyond). Chem Rev. 2015, 115(19): 11043-78.
Langut et al., 2013, Novel Targeted Therapy for Prostate Cancer, Poster abstract, 5th Annual Meeting Israel Society for Cancer Research, May 23, 2013.
Lemos-Gonzalez et al., Alteration of the serum levels of the epidermal growth factor receptor and its ligands in patients with non-small cell lung cancer and head and neck carcinoma, British Journal of Cancer (2007) 96, 1569-1578.

(56) References Cited

OTHER PUBLICATIONS

Levitzki, "EGF receptor as a therapeutic target," Lung Cancer, 2003, 41, S9-S14.
Levitzki et al., "Signal transduction therapy of cancer," Molecular Aspects of Medicine 31 (2010) 287-329.
Lin Z and Mahato R. Lipid and polymeric carrier-mediated nucleic acid delivery. Expert Opin Drug Deliv. Oct. 2010; 7(10): 1209-1226.
Milhaud et al., Antibody targeted liposomes containing poly(rI) • poly(rC) exert a specific antiviral and toxic effect on cells primed with interferons or α, β or γ, Biochimica et Biophysica Acta, 987 (1989) 15-20.
Ohno et al., Systemically Injected Exosomes Targeted to EGFR Deliver Antitumor MicroRNA to Breast Cancer Cells. Mol Ther. Jan. 2013;21(1):185-91.
Saul J et al., A dual-ligand approach for enhancing targeting selectivity of therapeutic nanocarriers. Journal of Controlled Release 114 (2006) 277-287.
Shi et al., Effect of Polyplex Morphology on Cellular Uptake, Intracellular Trafficking, and Transgene Expression, ACS Nano. 2013, vol. 7(12).
Shir et al., EGFR-Homing dsRNA Activates Cancer-Targeted Immune Response and Eliminates Disseminated EGFR-Overexpressing Tumors in Mice, Clin Cancer Res, 17(5) Mar. 1, 2011, pp. 1033-1043.
Shir et al., Gene Therapy for Glioblastoma: Future Perspective for Delivery Systems and Molecular Targets, Cellular and Molecular Neurobiology, vol. 21(6), 2001, pp. 645-656.
Shir et al., Inhibition of glioma growth by tumor-specific activation of double-stranded RNA-dependent protein kinase PKR, Nat Biotechnol. 2002, vol. 20(9), pp. 895-900.
Shir et al. "Nucleic Acid-Based Therapeutics for Glioblastoma," Anti-Cancer Agents in Medicinal Chemistry, 2011, 11, 1-7.
Singarapu et al., 2013, Polyethylene glycol-grafted polyethylenimine used to enhance adenovirus gene delivery. J Biomed Mater Res Part A 2013:101A, pp. 1857-1864.
Song E et al., Antibody mediated delivery of small interfering RNAs via cell-surface receptors. Nature Biotechnology, 23 (2005) 709-717.
Turner J et al., RNA targeting with peptide conjugates of oligonucleotides, siRNA and PNA. Blood Cells, Molecules, and Diseases 38 (2007) 1-7.
Wagner E. Tumor-targeted Delivery of Anti-microRNA for Cancer Therapy: pHLIP is Key. Angew. Chem. Int. Ed. 2015, 54, 2-5.
Yinxia Wu, Delivery of EZH2-shRNA with mPEG-PEInanoparticles for the treatment of prostate cancer in vitro, International Journal of Molecular Medicine 33: 1563-1569, 2014.
Zigler et al., Abstract B243: Targeting HER-2 positive breast cancer by inducing apoptosis and immune cell activation, overcoming trastuzumab resistance, Molecular Cancer Therapeutics, 2013, vol. 12, No. 11.
Zigler et al., HER2-Targeted Polyinosine/Polycytosine Therapy Inhibits Tumor Growth and Modulates the Tumor Immune Microenvironment, Cancer Immunol Res; 4(8) Aug. 2016.
Zigler et al., Targeted cancer immunotherapy, Current Opinion in Pharmacology 2013, vol. 13, pp. 504-510.

* cited by examiner

POLYPLEX OF DOUBLE-STRANDED RNA AND POLYMERIC CONJUGATE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application is a continuation of U.S. patent application Ser. No. 15/310,735 filed Nov. 11, 2016, which is the U.S. National Phase of International Application No. PCT/IL2015/050514 filed May 14, 2015, designating the U.S. and published in English as WO 2015/173824 A1 on Nov. 19, 2015 which claims the benefit of U.S. Provisional Application No. 61/993,110, filed on May 14, 2014, the disclosure of each of which is incorporated herein in its entirety by reference.

REFERENCE TO SEQUENCE LISTING

The present application is being filed along with a Sequence Listing in electronic format. The Sequence Listing is provided as a file entitled LSPA001_001C1.TXT, created Nov. 11, 2016, which is 3.14 kb in size. The information in the electronic format of the Sequence Listing is incorporated herein by reference in its entirety.

FIELD OF INVENTION

The present invention relates to non-viral polyethylenimine-based polyplexes conjugated to a targeting moiety capable of binding to a cancer antigen.

BACKGROUND OF THE INVENTION

One of the hurdles facing molecular medicine is the targeted delivery of therapeutic agents such as DNA or RNA molecules. An emerging strategy is the construction of non-viral vectors, such as cationic polymers and cationic lipids, which bind and condense nucleic acids. These non-viral cationic vectors possess many advantages over viral gene vectors, as they are non-immunogenic, non-oncogenic and easy to synthesize [1-4]. Currently, several synthetic polycationic polymers are being developed for nucleic acid delivery. Among these, polyethylenimines (PEIs) are considered promising agents for gene delivery [5].

PEIs are water-soluble, organic macromolecules that are available as both linear and branched structures [6]. PEIs change their degree of ionization over a broad range of pH, since every third atom in their backbone chain is an amino nitrogen, that can be protonated. Approximately 55% of the nitrogens in PEIs are protonated at physiological pH [7]. They possess high cationic charge density, and are therefore capable of forming non-covalent complexes with nucleic acids. Furthermore, their physicochemical and biological properties can be altered by various chemical modifications [8]. PEI-based complexes (also known as polyplexes) can be endocytosed by many cell types [9]. Following internalization of the polyplexes, endosome release and high efficiency gene transfer are driven by the "proton sponge effect" [10]. The ability of PEI to condense DNA appears to be an important factor in delivering large DNA constructs into many cell types.

The major concern in the utilization of PEIs as delivery carriers is toxicity, due to their high positive surface charge, which may lead to non-specific binding [11]. Recent attempts have been made to improve the selectivity and biocompatibility of non-viral vectors. This has led to the modification of PEI molecules with polyethylene glycol (PEG), in order to shield the PEI particle [12]. The conjugation of heterobifunctional PEG groups to PEI facilitates coupling of the PEI to a targeting ligand, which provides efficient gene delivery into cells harboring the cognate receptor [12]. We have previously described the generation of targeting vectors, demonstrating the difference between branched PEI (brPEI-EGF) and linear PEI (LPEI) tethered to EGF as targeting vectors [13, WO 2004/045491, WO 2010/073247]. Current methods of synthesis are unsatisfactory in that they result in insufficiently homogeneous products. There is thus a pressing need for methods that can provide efficient conjugation of targeting moieties to the LPEI-PEG in a reproducible manner to produce homogenous batches of products that can be reliably used in methods for treating cancer.

SUMMARY OF INVENTION

In one aspect, the present invention is related to a polyplex of a double stranded RNA (dsRNA) and a polymeric conjugate, wherein said polymeric conjugate consists of a linear polyethyleneimine (LPEI) covalently linked to one or more polyethylene glycol (PEG) moieties, each PEG moiety being conjugated via a linker to a targeting moiety capable of binding to a cancer antigen, provided that the targeting moiety is not mouse EGF (mEGF) or the peptide of the sequence YHWYGYTPQNVI (GE11) (SEQ ID NO: 1).

In another aspect, the present invention provides a pharmaceutical composition comprising a pharmaceutically acceptable carrier and a polyplex of the present invention as defined herein.

In yet another aspect, the present invention provides the polyplex of the present invention as defined herein, or the pharmaceutical composition comprising the polyplex, for use in treatment of a cancer selected from a cancer characterized by EGFR-overexpressing cells, a cancer characterized by HER2-overexpressing cells and prostate cancer.

In still another aspect, the present invention is related to a method for treating a cancer selected from the group consisting of a cancer characterized by EGFR-overexpressing cells, a cancer characterized by HER2-overexpressing cells and prostate cancer, the method comprising administering to a subject in need a polyplex of the present invention as defined herein.

In a further aspect, the present invention is related to a pharmaceutical composition comprising a pharmaceutically acceptable carrier and the polyplex of the present invention, for treatment of a cancer selected from a cancer characterized by EGFR-overexpressing cells, a cancer characterized by HER2-overexpressing cells and prostate cancer.

The polyplex of the present invention may be used in combination with immune cells.

DETAILED DESCRIPTION OF THE INVENTION

Figure 1:
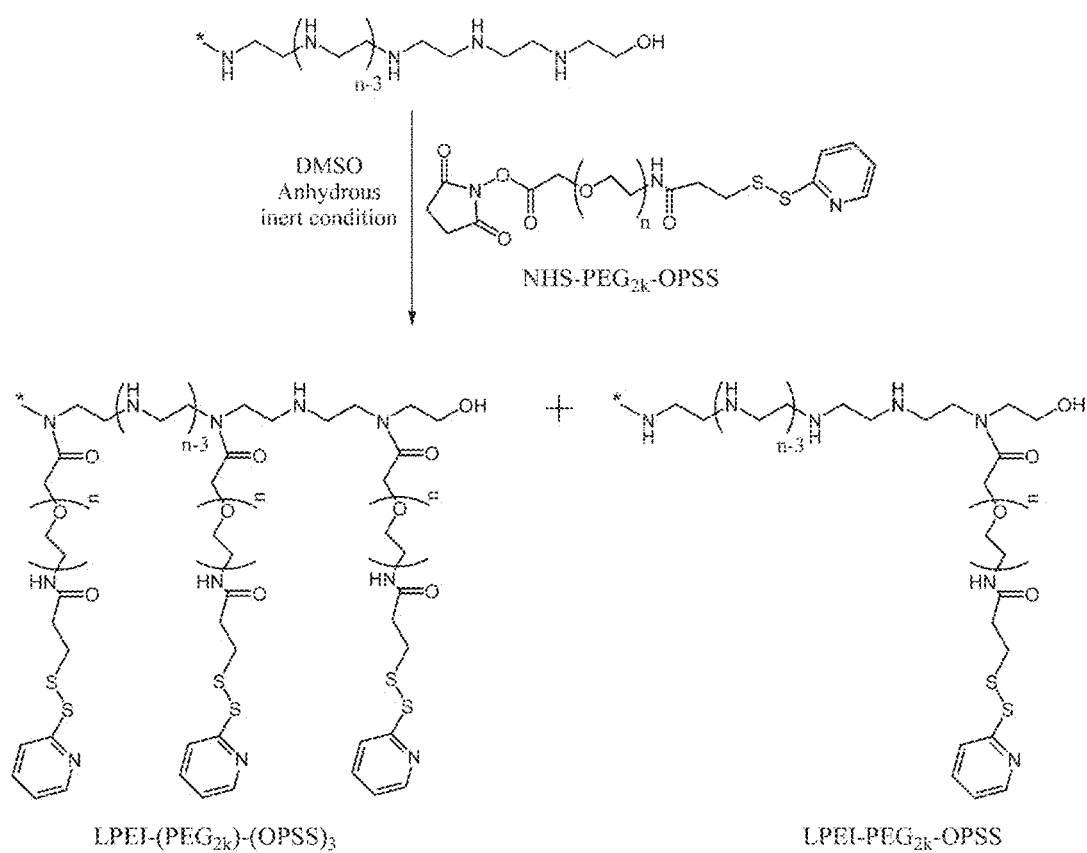
FIG. 1 shows that conjugation of LPEI (~22 kDa) with NHS-PEG-OPSS (~2 kDa) yielded mainly two co-polymeric networks that differ in the degree of PEGylation. The co-polymer LPEI-(PEG$_{2k}$-OPSS)$_3$ ("di-conjugate 1:3") consisted on average of 1 mole of LPEI and 3 moles of PEG, whereas co-polymer LPEI-PEG$_{2k}$-OPSS ("di-conjugate 1:1"), consisted on average of 1 mole ratio of LPEI and 1 mole of PEG. (Ratios of LPEI:PEG were determined by $^1$H-NMR analysis.)

Polycations, especially PEI, have been intensively investigated as agents for gene transfection. Optimal transfection efficacies are obtained when the polymeric nanoparticle complexes possess an overall positive charge, which allows them to bind to the negatively charged heparin sulfate proteoglycans on the cell surface [28]. Previous studies showed that linear PEI (LPEI) is more effective in gene transfection than branched PEI (brPEI) [29-31] [32, 33, WO 2010/073247], but that LPEI has higher positive charge and hence is more toxic. Various shielding entities, such as PEG [12], poly-(ethylene oxide)-poly(propylene oxide)-poly(ethylene oxide) (PEO-PPO-PEO) [18, 34] and poly(ethylene oxide) [35], have been conjugated to cationic polymers, in an attempt to lower the positive charge and the consequent toxicity. Indeed, shielding of PEIs with PEG groups of varying lengths significantly lowered toxicity while maintaining transfection efficiency [12, 13, 36].

It has been found in accordance with the present invention that the conjugation of LPEI with PEG2k yields di-conjugate co-polymers comprising various ratios of LPEI to PEG$_{2k}$. These di-conjugates could be separated from one another using cation exchange chromatography, due to differences in charge, which reflect the different numbers of PEG$_{2k}$ groups conjugated. $^1$H-NMR analysis confirmed that the di-conjugates differed from one another in the average number of PEG$_{2k}$ units per LPEI unit, where di-conjugate 1:1 had an LPEI:PEG$_{2k}$ ratio of 1:1 and di-conjugate 1:3 had an LPEI:PEG$_{2k}$ ratio of 1:3. The conjugation of the Her-2 targeting affibody to each of the purified di-conjugates yielded a tri-conjugate product of the appropriate molecular weight, i.e. from di-conjugate 1:1 we obtained "tri-conjugate 1:1" with LPEI:PEG$_{2k}$:Her-2 equal to 1:1:1 and from di-conjugate 1:3 we obtained "tri-conjugate 1:3", with ratio 1:3:3. This protocol enabled us to obtain homogeneous products, with nearly complete conjugation of targeting affibody to LPEI-PEG, in a reproducible manner.

We observed that PEGylation strongly affects the size of the polyplex particles obtained upon complexation of the di-conjugates or tri-conjugates with plasmid DNA. Both di-conjugate 1:3 and tri-conjugate 1:3 polyplexes had average particle sizes larger than di-conjugate 1:1 and tri-conjugate 1:1 polyplexes. We believe that increasing the amount of PEGylation on a single cationic chain leads to steric hindrance, which prevents the polymeric chain from condensing the plasmid to a smaller particle. This is consistent with the finding that the naked LPEI polyplex had the smallest particles. Moreover, while both tri-conjugates 1:1 and 1:3 protected complexed plasmid from DNase I, the tri-conjugated 1:3 polyplex provided better protection, possibly due to the increased steric hindrance.

Previous studies suggested that increasing the molecular weight of the PEG units conjugated to cationic polymers led to decreased surface charge of the polyplexes obtained upon complexation with nucleic acids [13]. Our data show that increasing the number of PEG groups of similar molecular weights leads to decreased surface charge, as defined by $\zeta$ potential distribution. Indeed, the highest surface charge was shown by naked LPEI complexed with plasmid. These results support the idea that the more neutral entities are present in a chemical vector, the lower the surface charge. Surprisingly, the tri-conjugate polyplexes conjugated to affibodies had lower surface charge than the di-conjugate polyplexes, showing that the Her-2 affibody (which itself has slight positive charge) also reduced the surface charge of the particles. We suspect that Her-2 affibody changes the topography of the particle with more targeting moieties masking the charge on the surface, leading to a decrease in surface charge.

The shape of a polyplex has a significant effect on its performance as a drug delivery candidate [37, 38], although it is not yet known which polyplex shapes are desirable for effective drug delivery. The effect of PEGylation on polyplex shape has not been investigated, to our knowledge, until now. In AFM pictures, the tri-conjugate 1:1 polyplex—which was more effective in gene delivery—presented shape homogeneity, while the tri-conjugate 1:3 was more heterogenic, with many asymmetrical, ellipsoidal particles.

Figure 10:
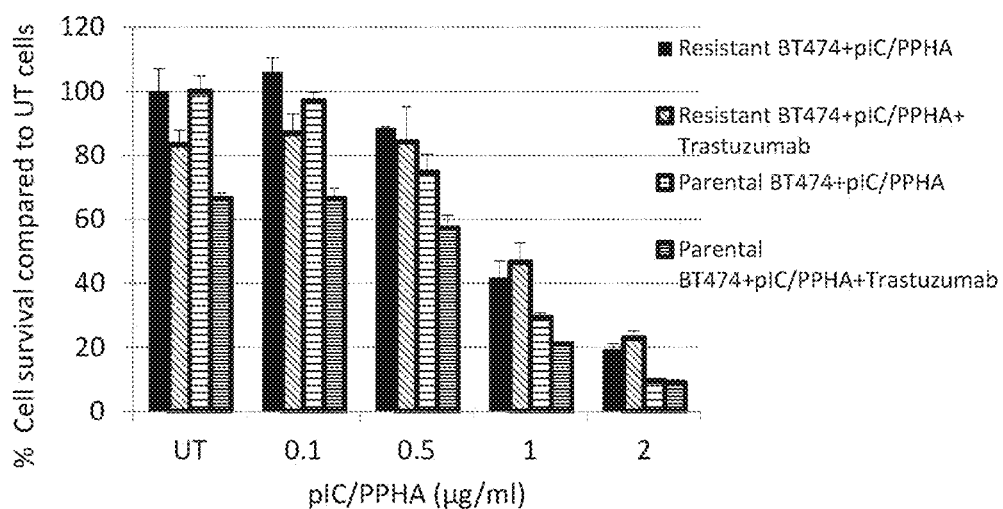
FIG. 10 shows that PEI-PEG-Her2Affibody (PPHA) complexed with PolyIC inhibits Her2 overexpressing breast cancer cells BT474. The complexed vector inhibits Her2 overexpressing cells, including Herceptin/trastusumab resistant cells.

Selective gene transfer using cationic polymers remains a major challenge. Previous studies have shown that targeting of LPEI and LPEI-PEG conjugates, with EGF or transferrin, increased their selectivity and decreased non-specific interactions both in vitro and in vivo [39, 40]. For example, to examine the selectivity of our Her-2 targeting tri-conjugates 1:1 and 1:3 polyplexes, we utilized two breast cancer cells that differentially express Her-2. Gene delivery, as shown by luciferase activity and GFP expression, was significantly higher in BT474 cells, which highly overexpress the Her-2 receptor, than in MDA-MB-231 cells, which express 100-fold less Her-2 receptors on the cell surface. Thus, the data demonstrate that both tri-conjugates 1:1 and 1:3 are highly selective for Her-2 overexpressing cells (FIG. 10).

Previous studies have shown that high levels of PEGylation can result in reduced gene transfection [41]. These results are in accordance with our observation that highly PEGylated tri-conjugate 1:3 polyplex showed a significant reduction in gene delivery, as compared to the less PEGylated tri-conjugate 1:1 polyplex, as shown by luciferase activity and GFP expression. The increased gene delivery by the lower PEGylated tri-conjugate 1:1 polyplex was accompanied by slight cellular toxicity, most likely due to its higher surface charge.

Our working hypothesis before engaging in this study was that increasing the number of targeting moieties per LPEI unit would lead to improved gene delivery and/or selectivity. We speculated that tri-conjugate 1:3, which has 3 moles of Her-2 affibody molecules conjugated per mole of LPEI, would show increased receptor-mediated particle internalization. However, the tri-conjugate 1:3 polyplexes showed lower $\zeta$ potential, larger particle size and heterogeneous, non-spherical shape, all of which characteristics might contribute to the decreased transfection efficiencies actually observed. Our results show that the less PEGylated tri-conjugate 1:1 is superior to the more PEGylated tri-conjugate 1:3 in mediating selective and efficient gene delivery into Her-2 overexpressing cells.

It has been found in accordance with the present invention that PEGylation of LPEI-based polyplexes leads to decreased surface charge, increased polyplex size and increased shape heterogeneity, and that these properties can have profound effects on targeted gene delivery. Our simplified synthesis allows purification of homogeneous products in a reproducible fashion, which can now be expanded to generate different tri-conjugates, using a variety of targeting moieties.

In view of the above, the present invention, in one aspect, provides a polyplex of a double stranded RNA (dsRNA) and a polymeric conjugate, wherein said polymeric conjugate consists of a linear polyethyleneimine (LPEI) covalently linked to one or more polyethylene glycol (PEG) moieties, each PEG moiety being conjugated via a linker to a targeting moiety capable of binding to a cancer antigen, provided that the targeting moiety is not mEGF or the peptide of the sequence YHWYGYTPQNVI (GE11) (SEQ ID NO: 1).

In certain embodiments, the cancer antigen may be, but is not limited to, an epidermal growth factor receptor (EGFR), human epidermal growth factor receptor 2 (HER2), prostate surface membrane antigen (PSMA), an insulin-like growth factor 1 receptor (IGF1R), a vascular endothelial growth factor receptor (VEGFR), a platelet-derived growth factor receptor (PDGFR) or a fibroblast growth factor receptor (FGFR). The targeting moiety may be a native, natural or modified ligand or a paralog thereof, or a non-native ligand such as an antibody, a single-chain variable fragment (scFv), or an antibody mimetic such as an affibody, to any one of the cancer antigens. Affibodies are based on the Z domain (the immunoglobulin G binding domain) of protein A and unique binding properties are acquired by randomization of 13 amino acids located in two alpha-helices involved in the binding activity of the parent protein domain.

In certain embodiments, the dsRNA is polyinosinic-polycytidylic acid double stranded RNA (poly I:C), the polymeric conjugate consists of LPEI covalently linked to one PEG moiety (LPEI-PEG 1:1) or to three PEG moieties (LPEI-PEG 1:3), and the cancer antigen is EGFR, HER2 or PSMA.

The molecular weight of PEG may be in the range of 2 to 8 kDa, in particular 2 kDa; the molecular weight of LPEI may be in the range of 10 to 30 kDa, in particular 22 kDa; and the polyIC of the polyplex of the invention may be composed of RNA strands each comprising at least 22, preferably at least 45 ribonucleotides. In certain embodiments, each strand has a number of ribonucleotides within the range of 20 to 300.

In certain embodiments, the one or more PEG moieties each independently forms —NH—CO— bond with the LPEI and a bond selected from —NH—CO—, —CO—NH—, —S—C—, —S—S—, —O—CO— or —CO—O— with the linker. In particular, each one of the one or more PEG moieties forms —NH—CO— bonds with the LPEI and the linker.

In certain embodiments, the linker forms an —S—S—, —NH—CO—, —CO—NH—, —S—C—, O—CO—, —CO—O— or urea (—NH—CO—NH) bond with the targeting moiety. The linker may be selected from —CO—$R_2$—$R_x$—$R_3$ or a peptide moiety consisting of 3 to 7 amino acid residues, wherein $R_2$ is selected from $(C_1$-$C_8)$alkylene, $(C_2$-$C_8)$alkenylene, $(C_2$-$C_8)$ alkynylene, $(C_6$-$C_{10})$arylene-diyl, or heteroarylenediyl;

$R_x$ is absent or —S—;

$R_3$ is absent or of the formula

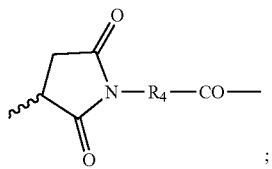
;

$R_4$ is selected from $(C_1$-$C_8)$alkylene, $(C_2$-$C_8)$alkenylene, $(C_2$-$C_8)$ alkynylene, $(C_1$-$C_8)$alkylene-$(C_3$-$C_8)$cycloalkylene, $(C_2$-$C_8)$alkenylene-$(C_3$-$C_8)$cycloalkylene, $(C_2$-$C_8)$ alkynylene-$(C_3$-$C_8)$cycloalkylene, $(C_6$-$C_{10})$arylene-diyl, heteroarylenediyl, $(C_1$-$C_8)$alkylene-$(C_6$-$C_{10})$arylene-diyl, or $(C_1$-$C_8)$alkylene-heteroarylenediyl;

wherein each one of said $(C_1$-$C_8)$alkylene, $(C_2$-$C_8)$alkenylene, or $(C_2$-$C_8)$ alkynylene is optionally substituted by one or more groups each independently selected from halogen, —$COR_5$, —$COOR_5$, —$OCOOR_5$, —$OCON(R_5)_2$, —CN, —$NO_2$, —$SR_5$, —$OR_5$, —$N(R_5)_2$, —$CON(R_5)_2$, —$SO_2R_5$, —$SO_3H$, —S(=O)$R_5$, $(C_6$-$C_{10})$aryl, $(C_1$-$C_4)$alkylene-$(C_6$-$C_{10})$aryl, heteroaryl, or $(C_1$-$C_4)$alkylene-heteroaryl, and further optionally interrupted by one or more identical or different heteroatoms selected from S, O or N, and/or at least one group each independently selected from —NH—CO—, —CO—NH—, —$N(R_5)$—, —$N(C_6$-$C_{10}$aryl)—, $(C_6$-$C_{10})$arylene-diyl, or heteroarylenediyl; and $R_5$ is H or $(C_1$-$C_8)$alkyl.

In certain embodiments, $R_2$ is selected from $(C_1$-$C_8)$ alkylene, preferably $(C_1$-$C_4)$alkylene, optionally substituted by one or more groups each independently selected from halogen, —COH, —COOH, —OCOOH, —$OCONH_2$, —CN, —$NO_2$, —SH, —OH, —$NH_2$, —$CONH_2$, —$SO_2H$, —$SO_3H$, —S(=O)H, $(C_6$-$C_{10})$aryl, $(C_1$-$C_4)$alkylene-$(C_6$-$C_{10})$aryl, heteroaryl, or $(C_1$-$C_4)$alkylene-heteroaryl, and further optionally interrupted by one or more identical or different heteroatoms selected from S, O or N, and/or at least one group each independently selected from —NH—CO—, —CO—NH—, —NH—, —$N(C_1$-$C_8$alkyl)—, —$N(C_6$-$C_{10}$aryl)—, $(C_6$-$C_{10})$arylene-diyl, or heteroarylenediyl. In particular, $R_2$ is selected from $(C_1$-$C_8)$alkylene, preferably $(C_1$-$C_4)$alkylene.

In certain embodiments, Rx is —S—.

In certain embodiments, $R_3$ is absent or

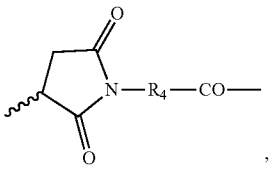
, wherein $R_4$ is $(C_1$-$C_8)$alkylene-$(C_3$-$C_8)$cycloalkylene, preferably $(C_1$-$C_4)$alkylene-$(C_5$-$C_6)$cycloalkylene.

In certain embodiments, in the polyplex as defined above, $R_2$ is —$CH_2$—$CH_2$—; $R_x$ is —S—; and $R_3$ is absent or

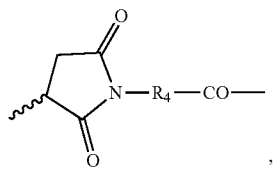
, wherein $R_4$ is

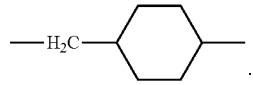
.

In certain embodiments, the linker is a peptide moiety comprising at least one, in particular two or three, aromatic amino acid residues such as phenylalanine, tryptophan, tyrosine or homophenylalanine. In certain embodiments, the peptide moiety is —(NH—$(CH_2)_7$—CO)-Phe-Gly-Trp-Trp-Gly-Cys-(SEQ ID NO: 2) or —(NH—$(CH_2)_7$-CO)-Phe-Phe-(NH—$CH_2$—CH($NH_2$)-CO)-Asp-Cys-(SEQ ID NO: 3), linked via its mercapto group to the targeting moiety.

In certain embodiments, the polymeric conjugate is a diconjugate of the formula (i)-(viii), linked to the targeting moiety/moieties:

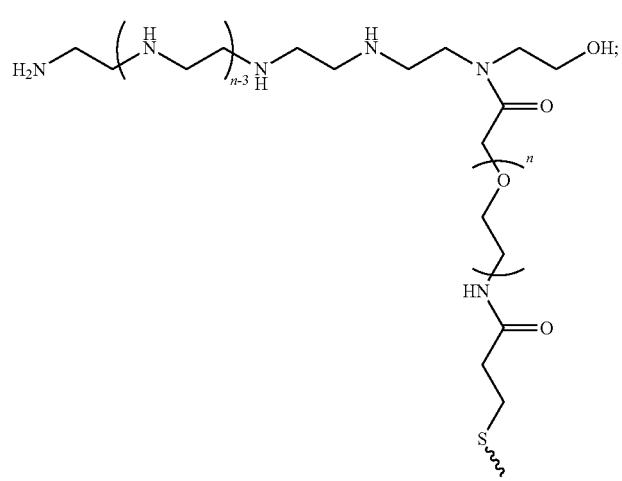
(i)
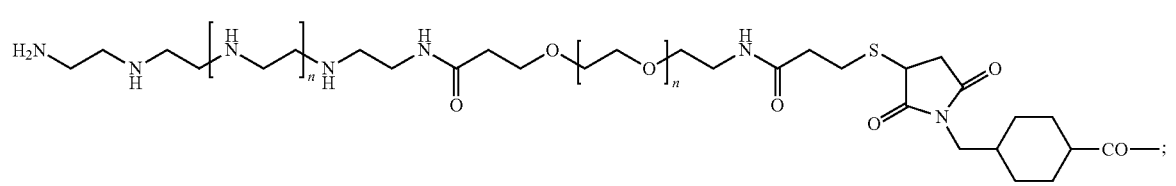
(ii)
—(NH—(CH$_2$)$_7$—CO)-Phe-Phe—(NH—CH$_2$—CH(NH$_2$)—CO)-Asp-Cys-PEG$_{2k}$-LPEI; (iii)
—(NH—(CH$_2$)$_7$—CO)-Phe-Gly-Trp-Trp-Gly-Cys-PEG$_{2k}$-LPEI; (iv)
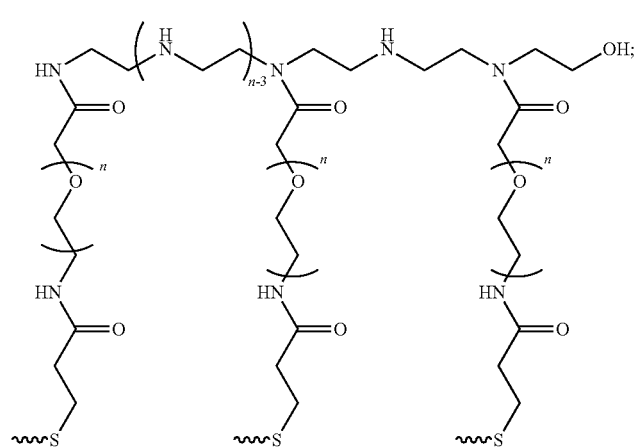
(v)

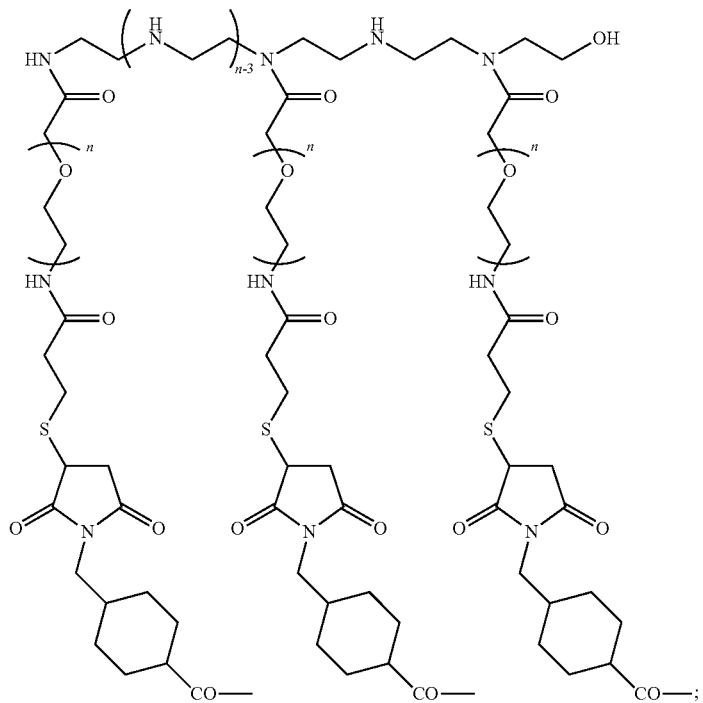
(vi)
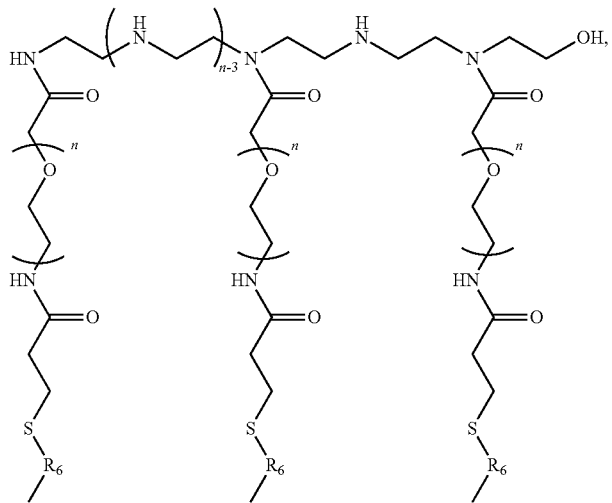
(vii)
wherein R$_6$ is
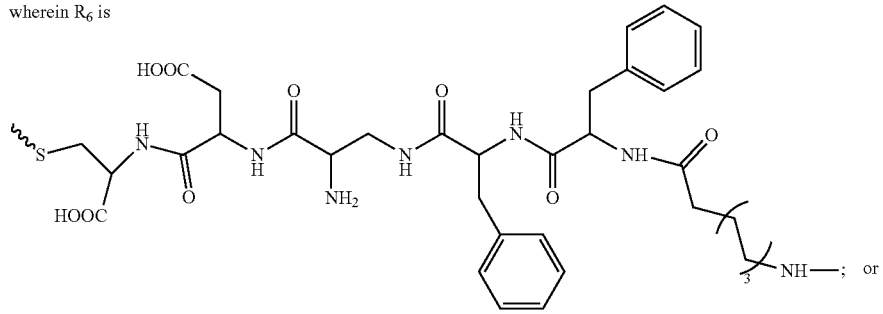

-continued (viii)

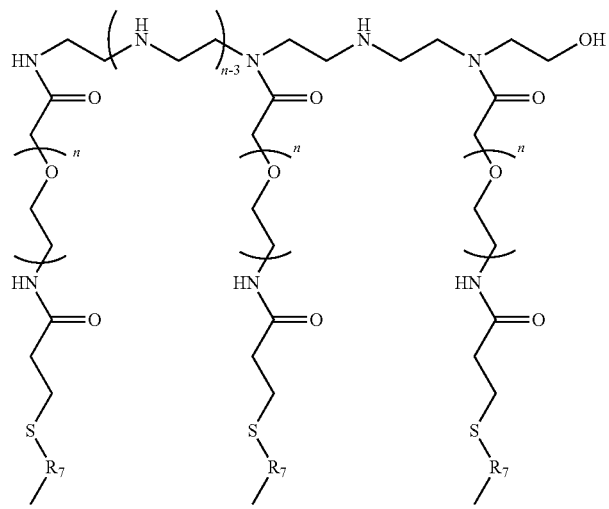

wherein R₇ is

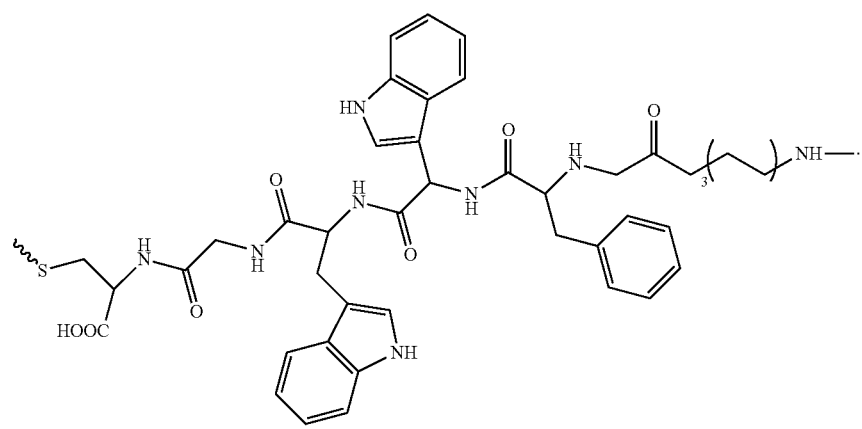

In particular embodiments, the polyplex is selected from
(a) the polyplex, wherein the targeting moiety is HER2 affibody, and the polymeric conjugate is of the formula (i) above, and the HER2 affibody is linked via a mercapto group thereof, herein also referred to as LPEI-PEG$_{2k}$-HER2;
(b) the polyplex, wherein the targeting moiety is HER2 affibody, and the polymeric conjugate is of the formula (v) above, and the HER2 affibody is linked via a mercapto group thereof, herein also referred to as LPEI-(PEG$_{2k}$-HER2)$_3$;
(c) the polyplex, wherein the targeting moiety is EGFR affibody, and the polymeric conjugate is of the formula (i) above, and the EGFR affibody is linked via a mercapto group thereof, herein also referred to as LPEI-PEG$_{2k}$-EGFR;
(d) the polyplex, wherein the targeting moiety is EGFR affibody, and the polymeric conjugate is of the formula (v) above, and the EGFR affibody is linked via a mercapto group thereof, herein also referred to as LPEI-(PEG$_{2k}$-EGFR)$_3$;
(e) the polyplex, wherein the targeting moiety is human EGF (hEGF), and the polymeric conjugate is of the formula (ii) above, and wherein the hEGF is linked via an amino group thereof, herein also referred to as LPEI-PEG$_{2k}$-hEGF;
(f) the polyplex, wherein the targeting moiety is hEGF, and the polymeric conjugate is of the formula (vi) above, wherein the hEGF is linked via an amino group thereof, herein also referred to as LPEI-(PEG$_{2k}$-hEGF)$_3$;
(g) the polyplex, wherein the targeting moiety is HOOC (CH$_2$)$_2$—CH(COOH)—NH—CO—NH—CH (COOH)—(CH$_2$)$_2$—CO—(DUPA residue), and the polymeric conjugate is of the formula (iii) above;
(h) the polyplex, wherein the targeting moiety is HOOC (CH$_2$)$_2$—CH(COOH)—NH—CO—NH—CH (COOH)—(CH$_2$)$_2$—CO— (DUPA residue), and the polymeric conjugate is of the formula (vii) above;
(i) the polyplex, wherein the targeting moiety is HOOC (CH$_2$)$_2$—CH(COOH)—NH—CO—NH—CH (COOH)—(CH$_2$)$_2$—CO— (DUPA residue), and the polymeric conjugate is of the formula (iv) above; or
(j) the polyplex, wherein the targeting moiety is HOOC (CH$_2$)$_2$—CH(COOH)—NH—CO—NH—CH (COOH)—(CH$_2$)$_2$—CO— (DUPA residue), and the polymeric conjugate is of the formula (viii) above.

The size of the nanoparticles formed by the polyplex of the present invention may be in the range of 120 to 150 nm, in particular 135-148 nm, or 142 nm.

Non-limiting examples of procedures for the preparation of polymeric conjugates used in the present invention are exemplified in Examples hereinafter.

In certain particular embodiments, the EGFR affibody is of the amino acid sequence as set forth in SEQ ID NO: 4, the HER2 affibody is of the amino acid sequence as set forth in SEQ ID NO: 5 and the hEGF is of the amino acid sequence as set forth in SEQ ID NO: 6.

In another aspect, the present invention relates to a pharmaceutical composition comprising a pharmaceutically acceptable carrier and the polyplex as defined above.

In yet another aspect, the present invention provides the polyplex of the present invention as defined herein, or the pharmaceutical composition comprising the polyplex, for use in treatment of a cancer selected from a cancer characterized by EGFR-overexpressing cells, a cancer characterized by HER2-overexpressing cells and prostate cancer.

In certain embodiments, the cancer characterized by EGFR-overexpressing cells is selected from non-small-cell-lung-carcinoma, breast cancer, glioblastoma, head and neck squamous cell carcinoma, colorectal cancer, adenocarcinoma, ovary cancer, bladder cancer or prostate cancer, and metastases thereof. In certain embodiments, the polyplex used for treatment of cancer characterized by EGFR-overexpressing cells is selected from the polyplex of (c), (d), (e) or (f) defined above.

In certain embodiments, the cancer characterized by HER2-overexpressing cells is selected from breast cancer, ovarian cancer, stomach cancer, and aggressive forms of uterine cancer, such as uterine serous endometrial carcinoma. In certain embodiments, the Her2 overexpressing cells are Herceptin/trastusumab resistant cells. Thus, the polyplex of the present invention may be for use in the treatment of Herceptin/trastusumab resistant cancer, i.e. cancer comprising cells that do not respond, or respond to a lesser extent to exposure to Herceptin/trastusumab.

In particular, the polyplex used for treatment of cancer characterized by HER2-overexpressing cells is selected from the polyplex (a), (b), (e) or (f) defined above.

In certain embodiments, the cancer is prostate cancer and the polyplex used for treatment of the prostate cancer is selected from (g), (h), (i) or (j) defined above.

In still another aspect the present invention is related to a method for treating a cancer selected from the group consisting of a cancer characterized by EGFR-overexpressing cells, a cancer characterized by HER2-overexpressing cells and prostate cancer, the method comprising administering to a subject in need a polyplex of the present invention as defined herein.

In a further aspect the present invention is related to a pharmaceutical composition comprising a pharmaceutically acceptable carrier and the polyplex of the present invention, for treatment of a cancer selected from a cancer characterized by EGFR-overexpressing cells, a cancer characterized by HER2-overexpressing cells and prostate cancer.

In yet a further aspect, the present invention is directed to the polyplex, the method, or the pharmaceutical composition of the present invention, for use in combination with immune cells.

In still a further aspect, the present invention is directed to a polyplex as defined herein above, in which the dsRNA is replaced with a DNA molecule, such as a plasmid comprising protein-encoding nucleic acid sequences operably linked to control elements such as appropriate promoters and terminators.

In certain embodiments, the immune cells are tumor-infiltrating T-cells (T-TILs), tumor specific engineered T-cells, or peripheral blood mononuclear cells (PBMCs).

The term "polyplex" as used herein refers to a complex between a nucleic acid and a polymer. The nucleic acid is bound to the polymer via non-covalent or covalent bonds, in particular electrostatic bonds. The term "polyplex" refers to a vector, i.e. a non-viral vector, useful for carrying and delivering nucleic acids into cells.

The term "patient", "subject", or "individual" are used interchangeably and refer to either a human or a non-human animal.

The term "$(C_1-C_8)$alkyl", as used herein, typically means a straight or branched hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like.

The term "$(C_1-C_8)$alkylene" refers to a straight or branched divalent hydrocarbon radical having 1-8 carbon atoms and includes, e.g., methylene, ethylene, propylene, butylene, pentanylene, hexanylene, heptanylene, octanylene, and the like. The term "$(C_2-C_2)$alkenylene" and "$(C_2-C_8)$alkynylene" typically mean straight or branched divalent hydrocarbon radicals having 2-8 carbon atoms and one or more double or triple bonds, respectively. Non-limiting examples of such radicals include ethenylene, propenylene, 1- and 2-butenylene, 1- and 2-pentenylene, 1-, 2- and 3-hexenylene, 1-, 2- and 3-heptenylene, 1-, 2-, 3- and 4-octenylene, ethynylene, propynylene, 1- and 2-butynylene, 2-methylpropylene, 1-and 2-pentynylene, 2-methylbutylene, 1-, 2- and 3-hexynylene, 1-, 2- and 3-heptynylene, 1-, 2-, 3- and 4-octynylene and the like.

The term "$(C_6-C_{10})$aryl" denotes an aromatic carbocyclic group having 6-10 carbon atoms consisting of a single ring or condensed multiple rings such as, but not limited to, phenyl and naphthyl; the term "$(C_6-C_{10})$arylene-diyl" denotes a divalent aromatic carbocyclic group having 6-10 carbon atoms consisting of either a single ring or condensed multiple rings such as, but not limited to, phenylene and naphthylene.

The term "heteroaryl" refers to a radical derived from a 5-10-membered mono- or poly-cyclic heteroaromatic ring containing one to three, preferably 1-2, heteroatoms selected from N, O, or S. Examples of mono-cyclic heteroaryls include, without being limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-α]pyridyl, benzimidazolyl, benzthiazolyl, benzoxazolyl, pyrido[1,2-a]pyrimidinyl and 1,3-benzodioxinyl. The heteroaryl may optionally be substituted by one or more groups each independently selected from halogen, —OH, —COOH, —CN, —NO$_2$, —SH, or —CONH$_2$. It is to be understood that when a polycyclic heteroaryl is substituted, the substitution may be in any of the carbocyclic and/or heterocyclic rings. The term "heteroarylenediyl" denotes a divalent radical derived from a "heteroaryl" as defined herein by removal of two hydrogen atoms from any of the ring atoms.

The term "halogen" as used herein refers to fluoro, chloro, bromo or iodo.

The term "$(C_3-C_8)$cycloalkylene" denotes a mono- or bi-cyclic saturated divalent cyclic hydrocarbon radical containing three to eight carbons. Non-limiting examples of such radicals include 1,2-cyclopropane-diyl, 1,2-cyclobutane-diyl, 1,3-cyclobutane-diyl, 1,2-cyclopentane-diyl, 1,3-cyclopentane-diyl, 1,2-cyclohexane-diyl, 1,3-cyclohexane-diyl, 1,4-cyclohexane-diyl, 1,2-cycloheptane-diyl, 1,3-cycloheptane-diyl, 1,4-cycloheptane-diyl, 1,2-cyclooctanediyl, 1,3-cyclooctane-diyl, 1,4-cyclooctane-diyl, 1,5-cyclooctane-diyl, and the like.

The term "amino acid residue", as used herein, refers to any natural or synthetic, i.e., non-natural, amino acid residue in its both L- and D-stereoisomers. While a natural amino acid is any one of the twenty amino acid residues typically occurring in proteins, the term synthetic/non-natural amino acid refers to any amino acid, modified amino acid and/or an analog thereof, that is not one of the twenty natural amino acids. Non-limiting examples of natural amino acids include glycine, alanine, valine, leucine, isoleucine, lysine, valine, phenylalanine, glutamic acid, aspartic acid, asparagine, glutamine, arginine, histidine, proline, serine, tyrosine, methionine, threonine, and tryptophan. Examples of non-natural amino acids, without being limited to, include ornithine, homolysine, 2,4-diaminobutyric acid (DABA), 2,3-diaminopropionic acid (DAP), 8-aminooctanoic acid (EAO), homophenylalanine, homovaline, homoleucine, and the like.

Pharmaceutical compositions in accordance with the present invention may be formulated in conventional manner using one or more physiologically acceptable carriers and/or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for intra-brain administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, for example for nasal administration, the compositions according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments the pharmaceutical composition is formulated for administration by any known method as described above. Particular methods of administration contemplated here are intravenous and intra-brain (intracerebral) administration.

The pharmaceutical composition according to any one of the embodiments defined above may be formulated for intravenous, intra-brain (intracerebral), oral, intradermal, intramuscular, subcutaneous, transdermal, transmucosal, intranasal or intraocular administration.

The invention will now be illustrated by the following non-limiting Examples.

EXAMPLES

Material and Methods (M&M)
Chemicals

NHS-PEG-OPSS (Ortho-Pyridyldisulfide-Polyethyene glycol-N-Hydroxylsuccinimide ester), also named PDP-PEG-NHS (PDP: pyridyl dithio propionate), with molecular weight of ~2 kDa was purchased from Creative PEGworks (Winston, USA). Poly (2-ethyl-2-oxazoline), average molecular weight (Mn) ~50 kDa, and anhydrous dimethylsulfoxide (DMSO) were purchased from Sigma Aldrich (Israel). Absolute ethanol was purchased from Romical (Israel). All solvents were used without further purification.
Synthesis of ~22 kDa LPEI (Free Base Form)

The cationic polymer Linear Polyethyleneimine (LPEI) was synthesized as described previously [16]. Briefly, 8.0 g (0.16 mmols) of poly(2-ethyl-2-oxazoline) were hydrolyzed with 100 ml of concentrated HCl (37%) and refluxed for 48 h, yielding a white precipitate. Excess HCl was removed under reduced pressure and the remaining solid was dissolved in 50 ml of water and freeze-dried (5 g, 78%, $^1$H-NMR, $D_2$O-d6, 400 MHz: singlet 3.5 ppm). The resulting LPEI hydrochloride salt (4.5 g) was made alkaline by adding aqueous NaOH (3 M) and the resulting white precipitate was filtrated and washed with water until neutral. The solid was then dissolved in water and further lyophilized to give white solid (2 g, 81%).
Synthesis of LPEI-PEGA-OPSS di-conjugates 174 mg (8 μmol) of LPEI were dissolved in 2.7 ml of absolute EtOH and agitated at room temperature for 15 minutes. A 5-fold molar excess of OPPS-PEG2k-CONHS (79 mg, 39.5 μmol) was dissolved in 500 μL of anhydrous DMSO and introduced in small portions into the LPEI mixture. The reaction mix was agitated at ~800 rpm on a vortex stirrer at ambient temperature for 3 h. Different PEG-substituted LPEIs were separated by cation-exchange chromatography, using an HR10/10 column filled with MacroPrep High S resin (BioRad). The purity of the eluted fractions of the di-conjugates was assessed using reverse phase HPLC equipped with analytical Vydac C-8 monomeric 5 μm column (300 Å, 4.6×150 mm), using a linear gradient of 5%-95% acetonitrile over 25 min at 1 ml/min flow. The fractions with 95% purity or higher were combined. The combined fractions were further dialyzed against 20 mM HEPES pH 7.4. The ratio of $PEG_{2k}$ groups conjugated to LPEI in the di-conjugates was determined by $^1$H-NMR. The integral values of the hydrogens from the polyethylene —($CH_2$—$CH_2$—O)— and from the LPEI —($CH_2$—$CH_2$—NH)— were used to determine the ratio between the two conjugated co-polymers. Of the various products obtained from the cation-exchange, two products, LPEI-$PEG_{2k}$-OPSS (di-conjugate 1:1, with molar ration of LPEI to PEG ~1:1) and LPEI-$(PEG_{2k})_3$-$(OPSS)_3$ (di-conjugate 1:3, with molar ratio of ~1:3), were chosen for the generation of tri-conjugates. A copper assay was used to evaluate the co-polymer concentration [17]. Briefly, co-polymers were incubated with $CuSO_4$ (23 mg dissolved in 100 ml of acetate buffer) for 20 minutes and their absorbance at 285 nm was measured.

SDS-Polyacrylamide Gel Electrophoresis (SDS-PAGE) of Proteins

Samples (30 µL) were diluted in SDS protein sample buffer with or without 100 mM DTT and then applied to Tricine gel (13% polyacrylamide). Electrophoresis was performed using cathode buffer (0.1 M Tris, 0.1 M Tricine and 0.1% SDS pH 8.25) and anode buffer (0.21 M Tris pH 8.9) and protein bands were visualized by staining with Instant-Blue™

Affibody Expression and Purification

A Her-2 affibody gene was cloned into plasmid pET28a, generating a vector encoding Z:2891 affibody fused to an N-terminal hexahistidyl (His6) tag and a Cys residue at the C terminus. The affibody was expressed in *E. coli* BL21 (DE3) as follows: The cells were grown at 37° C. to $OD_{600}$~0.7. IPTG was added to a final concentration of 0.5 mM, followed by incubation at 30° C. for 4 h. The cell pellet was stored at −80° C. To purify the affibody, the cell pellet was resuspended in buffer A (20 mM HEPES pH 7.4, 500 mM NaCl, 10% glycerol, 10 mM imidazole and 2 mM β-mercaptoethanol) and disrupted using a Microfluidizer Processor M-110EHI according to the manufacturer's instructions. The soluble fraction was recovered by centrifugation at 12,000×g for 10 min at 4° C. The resulting fraction was loaded onto a Ni affinity column (Clontech, Mountain View, Calif.). Column was washed with buffer A for 14 column volumes (cv). Thereafter, a step gradient elution was performed using increasing concentrations of buffer B (20 mM HEPES pH 7.4, 500 mM NaCl, 10% glycerol, 500 mM Imidazole and 2 mM β-Mercaptoethanol); 6% buffer B for 5 cv, 10% buffer B for 1.5 cv, 30% buffer B for 2 cv. The bound protein was eluted with 100% buffer B for 5 cv (protein purification facility, Wolfson centre, Israel). The eluted fractions were then concentrated with an Amicon filter (3 kDa cutoff) and loaded onto Gel filtration column Superdex 30 prep grade (120 ml) (GE healthcare). The purified proteins were further analyzed by SDS-PAGE and confirmed using Western blot analysis with anti-affibody antibody (Abcam). The purity was further assessed by reverse phase HPLC (Merck-Hitachi model L-7100) as described previously.

Synthesis of PEI-PEG-ligand Affibody (Tri-conjugate 1:1 and 1:3)

4.97 mg of each di-conjugate (1:1 and 1:3) were dissolved in 940 µl 20 mM HEPES pH 7.4. Then, 3.4 mg of Her-2 affibody in HBS were added dropwise to the reaction. 4 ml of 20 mM HEPES plus 700 µL of acetonitrile (HPLC Grade) were introduced to the reaction mix for increased solubility. The reaction was further vortexed (800 rpm) at room temperature until $A_{343}$ indicated complete turnover. The resulting tri-conjugates were purified by cation exchange chromatography on a HR10/10 column filled with MacroPrep High S resin (BioRad) (using three step gradient elution of 20 mM HEPES pH 7.4 to 20 mM HEPES containing 3 M NaCl). The eluted fractions were introduced to analytical RP-HPLC to assess the purity of tri-conjugates, fractions with 95% purity and higher were combined and were kept at −80° C. The concentration of the tri-conjugate was determined by copper assay (as above). The amount of conjugated protein was determined by $A_{280}$ using Nano-Drop 2000.

Verification and Purity of Chemical Vectors Conjugated to Targeting Protein.

The tri-conjugates were electrophoresed on SDS-PAGE, and stained with InstantBlue™, to confirm the conjugation of the affibody to LPEI-$PEG_{2k}$. The purity of the tri-conjugates was confirmed by reverse phase HPLC, using an analytical Vydac C-8 monomeric 5 µm column (300 Å, 4.6×150 mm) at 1 ml/min while monitoring at 220 nm. A gradient elution with acetonitrile, 5%-95% in 25 min with triple distilled water (TDW) containing 0.1% TFA as mobile phase were used for the HPLC analysis.

Polyplex Formation

Plasmid pGreenFire1, encoding Firefly Luciferase and GFP (System Biosciences, Inc), was amplified in *E. coli* and purified by Qiagen Plasmid Maxi Kits (Qiagen, Valencia, Calif., USA) according to the manufacturer's protocol. The tri-conjugate 1:1 or tri-conjugate 1:3 were complexed with plasmid at a ratio of N/P=6 in HEPES buffer glucose (where N=nitrogen from LPEI and P=phosphate from DNA) generating two Polyplexes. To allow complete formation of the polyplexes particles, the samples were incubated for 30 min at room temperature. The final plasmid concentration in polyplexes samples was 100 µg/ml whereas for DNase protection assay and luciferase assay, the final concentration of the plasmid was 10 µg/ml.

ζ-Potential and Sizing Measurements

The sizes of the polyplex particles obtained after dispersal in HBG buffer were measured at 25° C., by dynamic light scattering using a Nano-ZS Zetasizer (Malvern, UK), using volume distribution calculation. The instrument is equipped with a 633 nm laser, and light scattering is detected at 173° by back scattering technology (NIBS, Non-Invasive Back-Scatter). Each sample was run in triplicate. ζ potential measurements were also performed at 25° C. using a Nano-ZS Zetasizer (Malvern, UK). The ζ potential was evaluated after incubation of polyplexes in HBG buffer (pH 7.4). Light scattering from the moving particles was detected at 17°, and the Smoluchowski Model was used to determine the value of the Henry's function.

Atomic Force Microscopy

For AFM measurements, polyplexes were placed on freshly cleaved Mica disks (V1 12 mm, Ted Pella USA). Imaging was carried out in HBG buffer at 25° C., using commercial AFM, a NanoWizard® 3 (JPK instrument, Berlin, Germany) with QI™ mode. Si3N4 (MSNL-10 series, Bruker) cantilevers with spring constants ranging from 10 to 30 pN nm-1 were calibrated by the thermal fluctuation method (included in the AFM software) with an absolute uncertainty of approximately 10%. QI™ settings were as follows: Z-length: 0.1 µm; applied force: 0.5 nN; speed: 50 µm/s.

DNase Protection Assay

DNase I protection assays were conducted as described previously [18]. Briefly, 1 µg of pGreenFire1 DNA alone, with polyplex 1:1 or with polyplex 1:3 was mixed in a final volume of 50 µl in HBS solution. Following 30 minutes incubation at room temperature, 2 µL of DNase I (2 unit) or PBS were added to 10 µL of each sample and incubated for 15 min at 37° C. DNase I activity was terminated by the addition of 5 µL of 100 mM EDTA for 10 min at room temperature. To dissociate the plasmid from the tri-conjugates, 10 µL of 5 mg/mL heparin (Sigma, St. Louis, Mo.)

were added, and the tubes were incubated for 2 h at RT. Samples were electrophoresed on an 0.8% agarose gel and stained with ethidium bromide. Images were acquired using a Gel Doc EZ Imager (Bio Rad Laboratories, Inc).

Cell Culture

Her-2 overexpressing BT474 cells were cultured in RPMI medium supplemented with 10% fetal bovine serum (FBS), $10^4$ U/L penicillin, and 10 mg/L streptomycin at 37° C. in 5% $CO_2$. MDA-MB-231 human breast carcinoma cells, were cultured in Leibovitz L-15 medium with 10% FBS, $10^4$ U/L penicillin, and 10 mg/L streptomycin at 37° C. without $CO_2$. Cell lines were from the ATCC and cell culture reagents were from Biological Industries, Bet Ha'emek, Israel.

Luciferase Assay and Confocal Microscopy

10000 BT474 and MDA-MB-231 cells were plated in triplicate in 96-well plates. Cells were treated with tri-conjugate 1:1 and tri-conjugate 1:3 complexed with plasmid 48 h following treatment, cells were washed with PBS and lysed with 30 µl of cell lysis buffer (Promega, Mannheim, Germany) per well. Luciferase activity was measured in 25 µl samples of the lysates, using the Luciferase Assay system (Promega) according to manufacturer's recommendations. Measurements were performed using a Luminoskan™ Ascent Microplate Luminometer (Thermo Scientific). Values, in relative light units (RLU), are presented as the mean and standard deviation of luciferase activity from the triplicate samples. Confocal microscopy (FV-1200 Olympus) was used to visualize the GFP, which was taken to reflect the internalization of plasmid pGreenFire1. Pictures were taken at ×10 magnification.

Quantification of Cell Viability

Cell viability was measured by means of a colorimetric assay using methylene blue, as described previously [19]. Briefly, 10000 BT474 and MDA-MB-231 cells were plated in triplicate in 96-well plates. The cells were treated with polyplexes 1:1 and 1:3 containing 1 µg/ml pGreenFire1. 48 h following treatment, the cells were fixed with 1% formaldehyde in PBS (pH 7.4), washed with DDW and then stained with a 1% (wt/vol) solution of methylene blue in borate buffer for 1 h. Thereafter, the stain was extracted with 0.1 M HCl and the optical density of the stain solution was read at 630 nm in a microplate reader (ELx800 BIO-TEX instruments Inc.).

Example 1

Synthesis of Thiol Reactive Co-polymers 3.1. Previous studies have demonstrated the PEGylation of LPEI and its conjugation to an EGFR targeting moiety [13]. However, the amount of PEGylation on a single LPEI chain has not been fully characterized. To generate differentially PEGylated co-polymers, the secondary amines on LPEI were conjugated to the terminal NHS ester orthogonal protecting group on PEG. The N-hydroxysuccinimide (NHS) ester is spontaneously reactive with the secondary backbone amines of LPEI, providing efficient PEGylation of LPEI. Furthermore, the reaction of the NHS-PEG OPSS with the amines of PEI results in formation of stable, irreversible amide bonds (FIG. 1).

Figure 2:
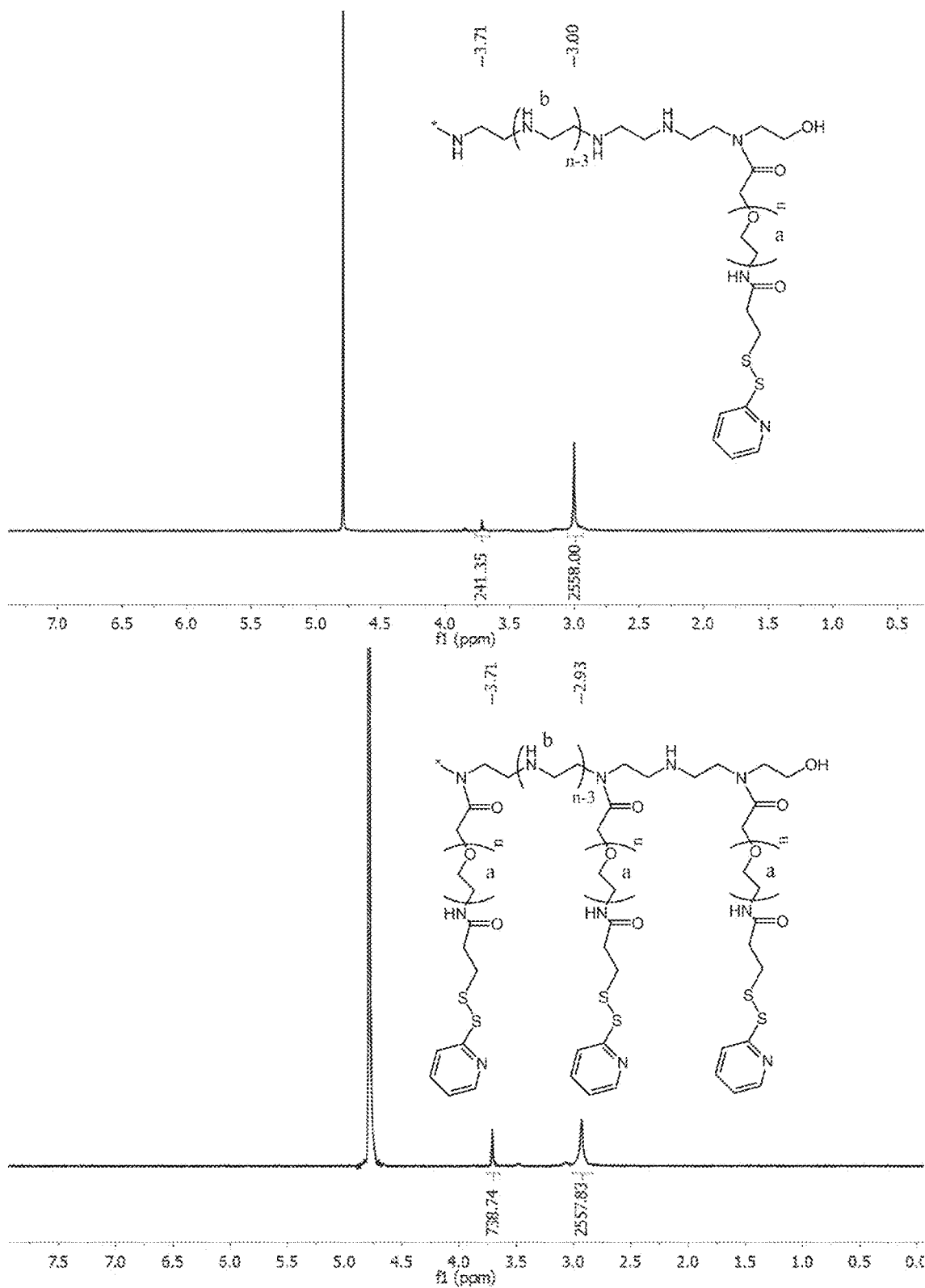
FIG. 2 shows $^1$H-NMR analysis of the two di-conjugates, LPEI-PEG$_{2k}$-OPSS (di-conjugate 1:1) and LPEI-(PEG2k-OPSS)3 (di-conjugate 1:3). The coupling of PEG groups to LPEI was indicated by the presence of the chemical shifts that correlate to ethylene glycol hydrogens (a) at 3.7 ppm and ethyleneimine hydrogens at ~3.0 ppm (b). The integral values of these peaks provide molar ratios of PEG to LPEI, from which the illustrated structures of di-conjugate 1:1 (A) and di-conjugate 1:3 (B) were deduced.

The PEGylation products were purified by cation exchange chromatography. Two peaks were eluted at high concentrations of NaCl, one at 120 mS/cm and the other at 132 mS/cm (data not shown). The two products were presumed to differ in their ratios of LPEI:PEG and consequently in their net positive charges. $^1$H-NMR spectra were analyzed using the relative integral values of the hydrogen atoms on PEG (—$CH_2$—$CH_2$—O—) (FIG. 2) and the integral values of the hydrogen atoms on LPEI (—$CH_2$—$CH_2$—NH—) (FIG. 2). This analysis indicated that the material eluted in the first peak consisted of a co-polymer in which each mole of LPEI was conjugated to approximately three moles of PEG. This product was named LPEI-($PEG_{2k}$) 3-(OPSS)3 ("di-conjugate 1:3"). The second peak consisted of a co-polymer in which equal moles of PEG were conjugated to LPEI, and was named LPEI-$PEG_{2k}$-OPSS ("di-conjugate 1:1") (FIG. 2).

Example 2

Synthesis of the Tri-conjugates, LPEI-$PEG_{2k}$-Her2 Affibody (Tri-conjugate 1:1) & LPEI-($PEG_{2k}$)-(Her2)$_3$ Affibody (Tri-conjugate 1:3)

Figure 3:
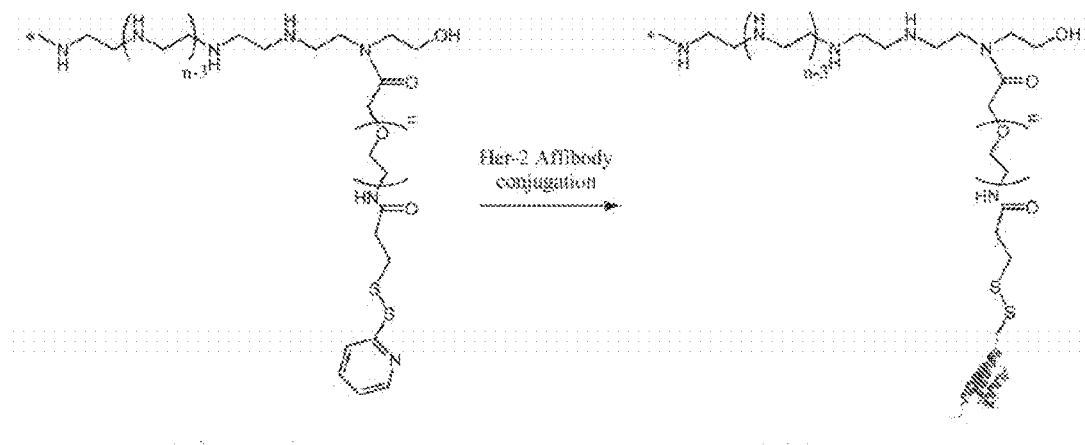
FIG. 3 shows a scheme for conjugation of the co-polymeric networks (di-conjugate 1:1 and di-conjugate 1:3) to the affibody ("Her-2") through disulfide exchange, resulting in the generation of two differently PEGylated tri-conjugates [20].
Figure 3:
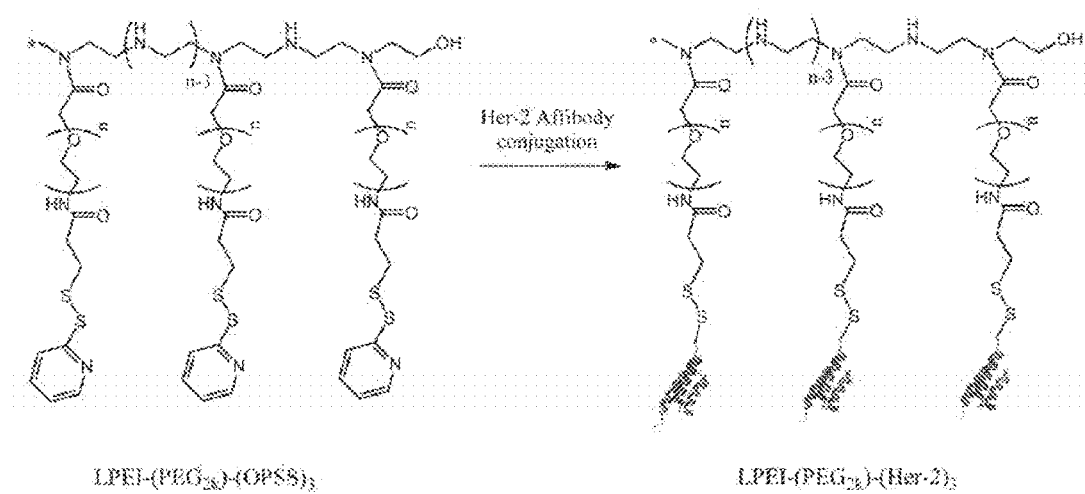
Figure 4:
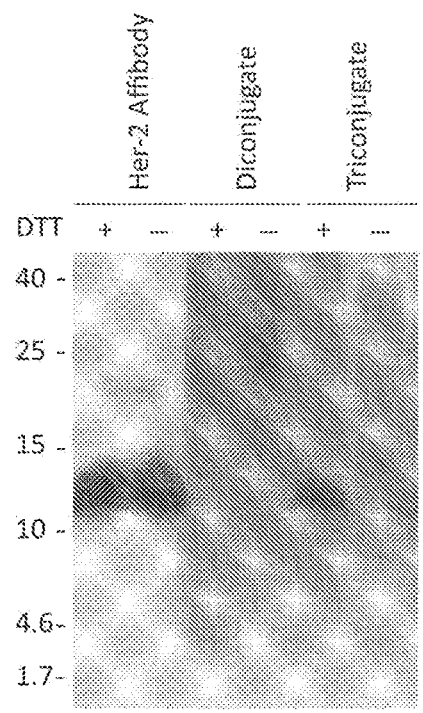
FIG. 4 depicts an SDS/PAGE of purified affibody, di-conjugate and tri-conjugate, in the absence and in the presence of DTT. In the presence of DTT, the affibody is released from the tri-conjugate, and migrates alongside purified affibody (slightly above 10 kDa).

The primary aim of this study was to develop a cationic polymer that would target Her-2 overexpressing tumor cells. Since Her-2 is an "orphan receptor", affibody molecules targeting the Her-2 receptor (rather than ligand) were used to generate Her-2 targeting tri-conjugates. We expressed and purified Her-2 affibody with a Cys residue at the C-terminal end to allow further conjugation. The thiol reactive co-polymers, di-conjugate 1:1 and 1:3, were conjugated to Her-2 affibody through its terminal Cys residue, generating tri-conjugates 1:1 and 1:3 respectively (FIG. 3). In order to generate the tri-conjugates the reaction had to be performed with low concentration of affibody (to prevent aggregation) and in the presence of 10% acetonitrile (ACN) as an organic polar solvent for increased solubility. The reaction yields for both tri-conjugate reactions were approximately 33% as determined by copper assay. To confirm the conjugation of the affibody to the di-conjugate, the tri-conjugate products were reduced with DTT and separated on SDS-PAGE. Coomassie blue staining confirmed that the reduced tri-conjugate released the affibody (FIG. 4). The amount of Her-2 affibody present in the tri-conjugates was determined by measuring $A_{280}$. Using copper assay, we quantified the LPEI. As described above, $^1$H-NMR analysis showed that the ratios of LPEI:PEG in the purified di-conjugates were 1:1 or 1:3. Comparing the molar ratios of Her-2 affibody and LPEI, we determined that the average ratio of Her-2 affibody to LPEI in tri-conjugate 1:1 was 1:1, and in tri-conjugate 1:3 the average ratio was 3:1. Thus we conclude that nearly complete conjugation of affibody to LPEI-PEG was achieved.

To generate polyplexes, the pure di-conjugates and tri-conjugates (1:1 and 1:3) were complexed with plasmid DNA, as described in the Materials and Methods (FIG. 3).

Example 3

ζ Potential and Sizing of Polyplexes

Figure 5:
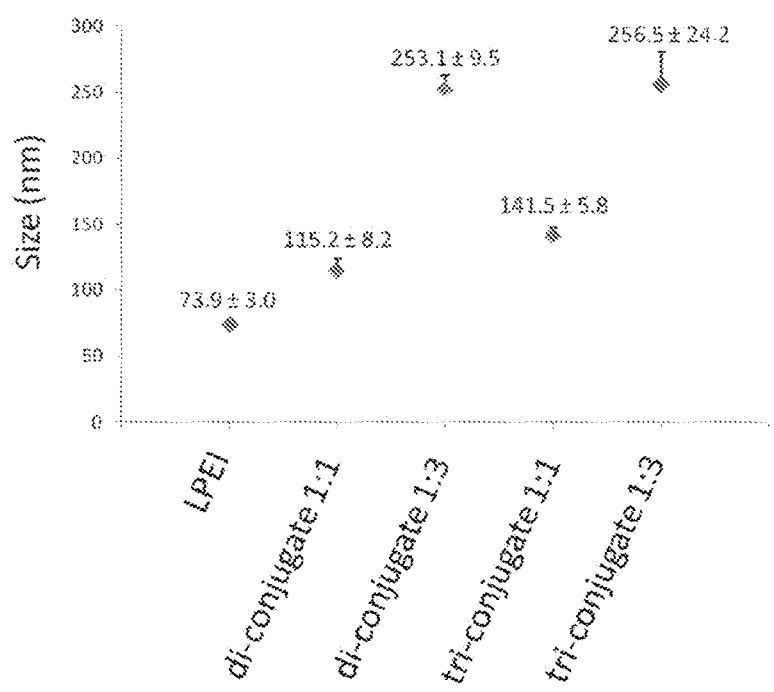
FIG. 5 shows particle sizing using DLS measurements of LPEI, the di-conjugates and the tri-conjugates complexed with plasmid pGreenfire 1 in HBG buffer pH 7.4.

We next characterized the polyplexes, with respect to size and surface charge, using dynamic light scattering (DLS). The size of a polyplex has a significant impact on its delivery properties [21]. In order to investigate the effect of targeting ligand on the size of a polyplex we decided to complex both di-conjugates 1:1 and 1:3 with plasmid and measure their size. Di-conjugate 1:1 had an average particle size of 115.2±8.2 nm and di-conjugate 1:3 had an average particle size of 253.1±9.5 nm. The polyplex generated from tri-conjugate 1:1 with plasmid gave an average particle size of 141±5.8 nm, whereas tri-conjugate 1:3 complexed with plasmid had an average particle size of 256±24.2 nm (FIG. 5). The smallest particles (73.9±3.0 nm) were obtained in polyplexes generated by complexing the plasmid with LPEI alone. The conjugation of the affibody to the di-conjugates had only a minor affect on the particle size. The number of PEG groups, however, did affect the particle size, suggesting that the PEG groups cause steric hindrance, interfering with plasmid condensation.

Figure 6:
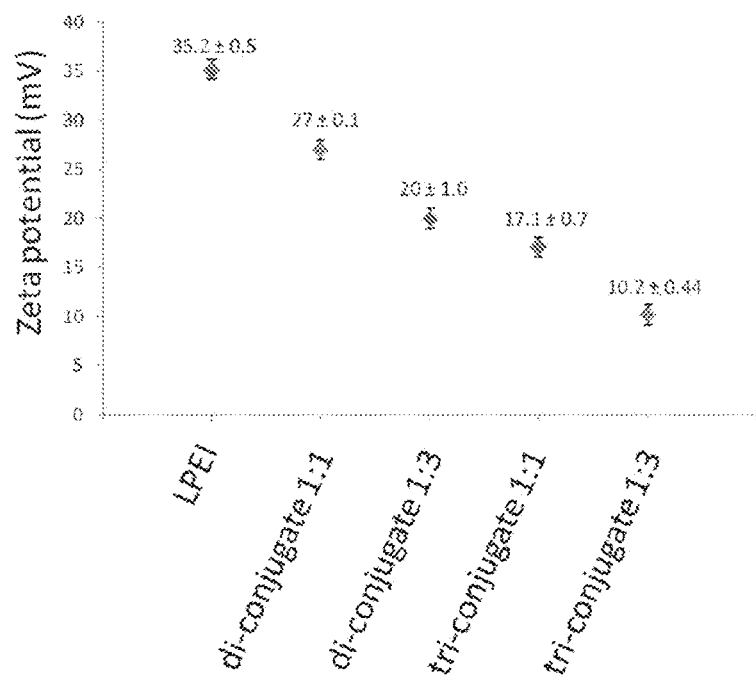
FIG. 6 depicts ζ potential distributions of LPEI, di-conjugates and tri-conjugates complexed with plasmid pGreenfire1. The zeta potentials were measured by DLS and calculated by the Smoluchowski equation.

A positive surface charge facilitates polyplex binding to the negatively charged cell surface, but excessive positive charge can lead to non-specific binding and significant toxicity [12]. The $\zeta$ potentials of the various complexes, presented in FIG. 6, are in agreement with previous studies, which showed a decrease in $\zeta$ potential with increased number of PEG units [13]. To assess the effect of PEG groups on the surface charge of our chemical vectors we measured the $\zeta$ potentials of polyplexes formed by complexation of plasmid DNA with the precursors, di-conjugates 1:1 and 1:3, and with the tri-conjugates 1:1 and 1:3. Di-conjugate polyplex 1:1 had an average $\zeta$ potential of 27.0±0.1 mV and di-conjugate polyplex 1:3 had an average $\zeta$ potential of 20.0±1.0 mV. Tri-conjugate polyplex 1:1 showed $\zeta$ potential with an average of 17.1±0.7 mV, whereas tri-conjugate polyplex 1:3 showed an average of 10.2±0.44 mV (FIG. 6). Unlike the sizes, the $\zeta$ potentials of the polyplexes were affected by both the number of PEG groups and the conjugation of the Her-2 affibody. Although the smallest, most positively charged polyplexes were obtained with naked LPEI, these particles are extremely toxic [22]. We expected that the addition of PEG groups and a targeting moiety would diminish toxicity, but because the polyplexes were still relatively small in size, we hoped that their efficiency as nucleic acid delivery vectors would not be compromised.

Example 4

Assessment of Polyplex Shape Using Atomic Force Microscopy

Figure 7A:
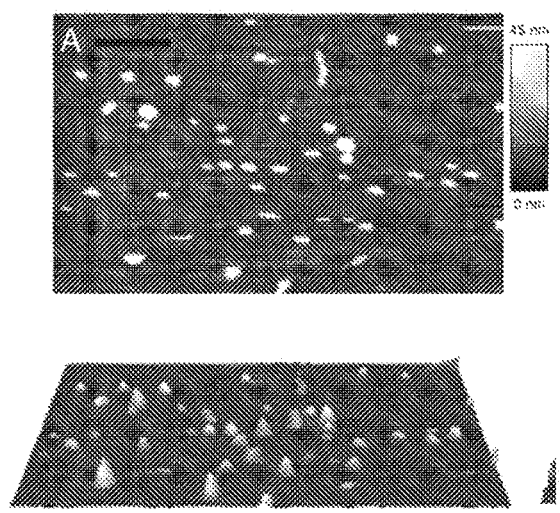
FIGS. 7A-B show atomic force microscopy (AFM) images obtained from measurements performed in HBG buffer pH 7.4 for both polyplexes. (A) tri-conjugate 1:1 Polyplex (B) tri-conjugate 1:3 Polyplex. Scale bar is
Figure 7B:
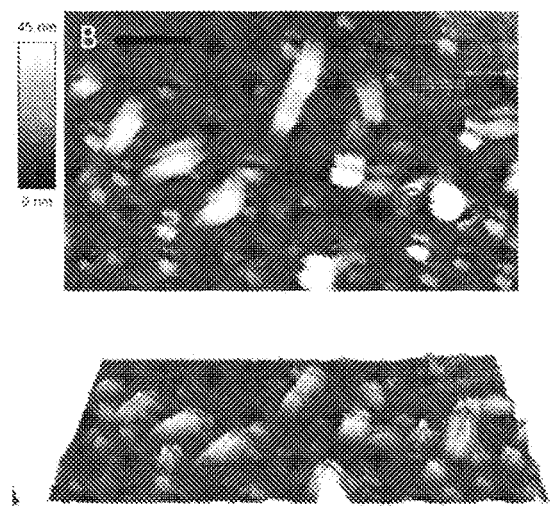

The importance of particle shape and its influence on delivery properties is gaining recognition [23]. We analyzed the morphology of the polyplexes obtained with the tri-conjugates in solution using Atomic Force Microscopy (AFM). The diameters of tri-conjugates 1:1 and 1:3 polyplexes were both in the nano-size range (FIGS. 7A-B), in agreement with the results obtained by DLS. The tri-conjugate 1:1 polyplex displayed mainly elliptical particles. Most particles ranged in diameter from 101 nm to 178 nm, with an average particle diameter of 142 nm. A few particles were exceptionally large, with some even reaching >250 nm (FIG. 7A). Tri-conjugate 1:3 polyplex was more heterogenic in shape, and moreover, yielded large aggregates with undefined particle shape (FIG. 7B). These ranged in length from 150 nm to 650 nm, with an average particle length of 312 nm and their width ranged from 85 nm to 400 nm, with an average width of 175 nm.

Example 5

DNAse Protection Assay

Figure 8:
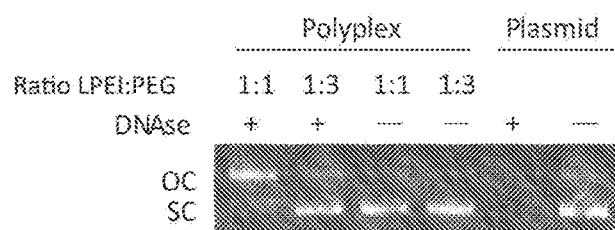
FIG. 8 depicts an agar gel showing that differentially PEGylated polyplexes protect plasmid pGreenFire1 from DNase I degradation. 1 μg plasmid (pGreenFire1) alone or in tri-conjugate polyplexes: 1:1 and 1:3 was treated with or without DNase I (2 IU). Supercoiled plasmid (s.c.), open circular plasmid (o.c.).

Successful in vivo gene delivery depends on efficient protection from nucleases. To determine the ability of the tri-conjugates to protect plasmids from degradation and enable efficient gene delivery, the polyplexes were treated with DNase I and analyzed using gel electrophoresis. As shown in FIG. 8, naked plasmid pGreenFire1 DNA was fully degraded following 10 minutes of incubation with 2 units of DNase I. In contrast, when polyplexes were generated by mixing plasmid with the tri-conjugates, the plasmid was protected from degradation by DNase I. Complete protection of the plasmid was observed for tri-conjugate polyplex 1:3, while some nicking did occur for tri-conjugate polyplex 1:1, as shown by the shift from the supercoiled (s.c.) to the open circular (o.c.) form of the plasmid. The stronger protection from DNase I conferred by tri-conjugate polyplex 1:3 may be attributed to the increased steric hindrance provided by the additional PEG-protein units in these complexes. Indeed, previous studies have shown that PEGylation of PEI can stabilize polyplexes and increase their circulation in the blood, by impeding their interactions with enzymes and serum factors [24, 25].

Example 6

Biological Activity of Targeting Tri-conjugate Polyplexes

Figure 9A:
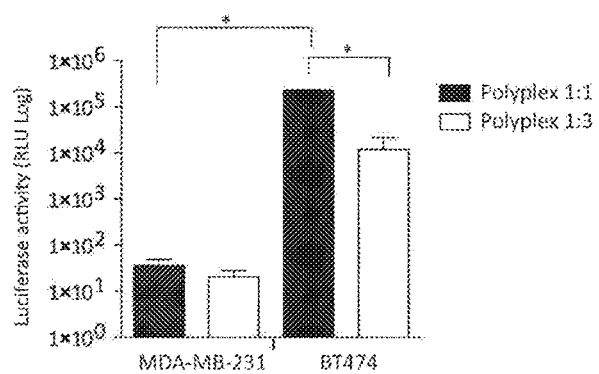
FIGS. 9A-C show Her-2 mediated gene transfer of pGFP-LUC using the tri-conjugate 1:1 polyplex and the tri-conjugate 1:3 polyplex containing LPEI:PEG ratios of 1:1 and 1:3 respectively. 10000 BT474 and MDA-MB-231 breast cancer cells/well were treated for 48 h with tri-conjugates 1:1 and 1:3 complexed with pGFP-LUC (1 μg/ml) to generate the two polyplexes. PEI nitrogen/DNA phosphate ratio of 6 (N/P=6) in HBS. (A) Measurements of luciferase activity demonstrate significant decreased pGreenFire1 delivery in MDA-MB-231 cells, compared to BT474 and reduced gene delivery mediated by tri-conjugate 1:3 polyplexes as compared to tri-conjugate 1:1 (*p<0.001). Luciferase activity was measured in triplicates after 48 h shown as relative lucifarese units (RLU) as mean+S.D. (B) Fluorescent images of cells treated with polyplexes. Images are shown at ×10 magnification and are representative of three experiments performed. (C) Methylene blue assay depicts percent of cell survival compared to untreated (UT) cells.
Figure 9B:
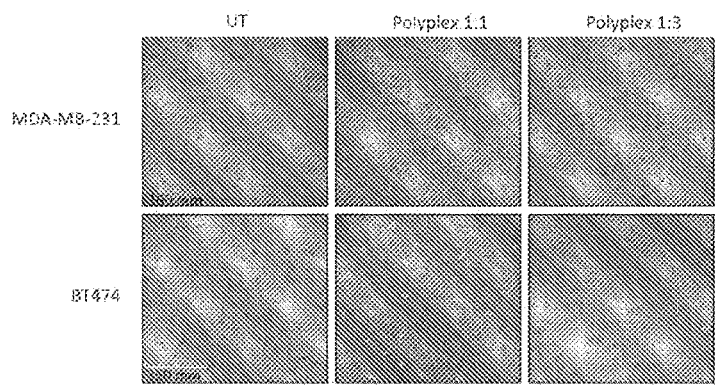

Polyplex size and $\zeta$ potential influence the efficiency of targeted DNA delivery and gene expression, but the effect of size appears to be dependent on the particular conjugate [2] [21]. To evaluate the specificity and the efficiency of transfection of the tri-conjugate polyplexes 1:1 and 1:3, two breast cancer cell lines that differentially express Her-2 were utilized. Polyplexes of the tri-conjugates 1:1 and 1:3 were formed with pGreenFire1 and transfected into MDA-MB-231 cells (expressing approximately $9 \times 10^3$ Her-2 receptors/cell [26]) and BT474 cells (expressing approximately $1 \times 10^6$ Her-2 receptors/cell [27]). Differential luciferase activity was observed 48 h after transfection. Both tri-conjugate polyplexes 1:1 and 1:3 led to more than 300-fold higher luciferase activity in BT474 cells than in MDA-MB-231 (*$p < 0.001$) (Figure. 9A). More efficient gene delivery to BT474 was confirmed by GFP expression, as seen by confocal microscopy (FIG. 9B). These results show that polyplex selectivity is dependent on Her-2 expression.

Targeted delivery to BT474 cells by tri-conjugate polyplex 1:1 was 10-fold more efficient than delivery by tri-conjugate polyplex 1:3 (FIG. 9A, B), even though tri-conjugate 1:3 has more targeting moieties. This may reflect the higher $\zeta$ potential and lower size of tri-conjugate polyplex 1:1.

Figure 9C:
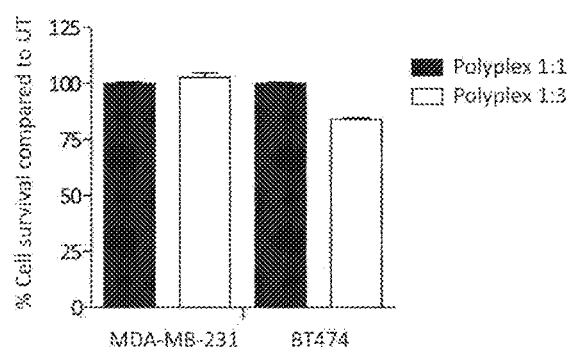

Positively charged LPEI-based chemical vectors are associated with significant toxicity. Therefore, we next tested the survival of MDA-MB-231 and BT474 cells following treatment with tri-conjugate polyplexes 1:1 and 1:3. Neither polyplex showed cytotoxic effects in MDA-MB-231 cells, in a methylene blue assay. Similar results were observed in BT474 cells treated with tri-conjugate polyplex 1:3. However, a slight increase in cell cytoxicity was observed in BT474 treated with tri-conjugate polyplex 1:1 (FIG. 9C). Altogether, these results indicate that the small size and higher $\zeta$ potential of tri-conjugate polyplex 1:1 confer efficient targeted delivery properties, with only a slight increase in toxicity. Thus, polyplex of the tri-conjugate 1:1 is superior in gene delivery to the more shielded tri-conjugate polyplex 1:3.

Example 7

Anti-tumor Activity of PEI-PEG-Her2Affibody

The PEI-PEG-Her2Affibody (PPHA) complexed with PolyInosine/PolyCytosine (PolyIC) has strong anti-tumor activity. Breast cancer cell lines overexpressing Her-2 were found to be strongly inhibited by a complex of PEI-PEG-Her2Affibody with PolyIC. Strong inhibition was observed also of trastuzumab resistant Her2 overexpressing breast cancer cell lines.

FIG. 10 shows that the vector/polyplex inhibits Her2 overexpressing cells, including Herceptin/trastusumab resistant cells.

Figure 11:
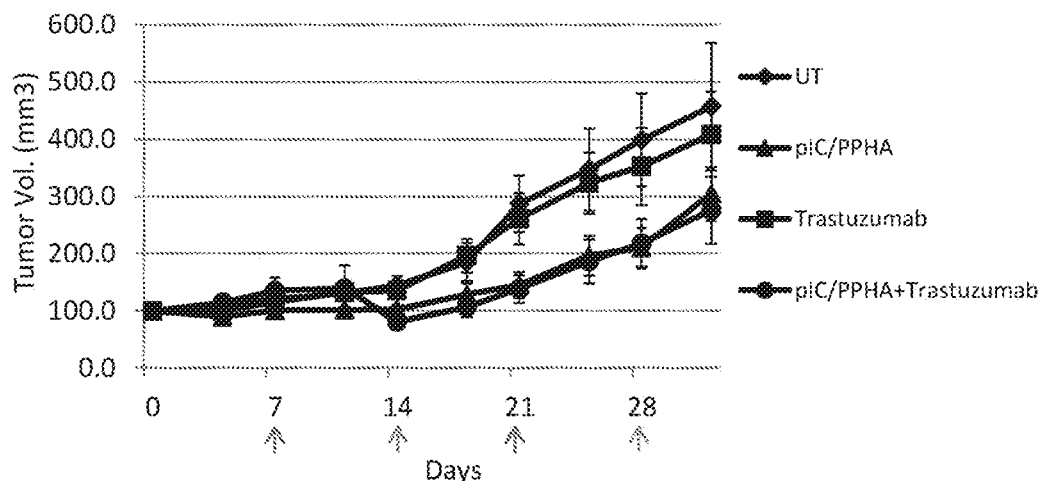
FIG. 11 shows inhibition of MCF7 cells overexpressing Her2 injected in nude mice.

$0.5 \times 10^6$ MCF-7 HER-2 cells were injected s.c. into mude mice. After tumors reached and average of 100 mm$^3$, treatment began. 1 mg/kg pIC/PPHA was injected i.v. at every 24 hrs. Trastuzumab was administered i.v. once a week (indicated by arrows), to two groups of mice. Tumor growth was measured twice a week. The complex PolyIC/PPHA was found to possess strong anti-tumor activity in mouse models in which these cell lines were implanted in nude mice as exemplified in FIG. 11.

Example 8

Synthesis of LPEI-PEG-EGFR Affibody 5 mg ($2 \times 10^{-4}$ mmol) of LPEI-PEG$_{2k}$-OPSS (di-conjugate 1:1) were dissolved in 1 ml 20 mM HEPES pH 7.4. Then, 3.4 mg ($3.8 \times 10^{-4}$ mmol, ~2 eq) of EGFR affibody in HBS were added dropwise to the reaction. 4 ml of 20 mM HEPES plus 700 µL of acetonitrile (HPLC Grade) were introduced to the reaction mix for increased solubility. The reaction was further vortexed (800 rpm) at room temperature and dark conditions until $A_{343}$ indicated complete turnover. The resulting tri-conjugate was purified by cation exchange chromatography on a HR10/10 column filled with Macro-Prep High S resin (BioRad) (using three step gradient elution of 20 mM HEPES pH 7.4 to 20 mM HEPES containing 3 M NaCl). The eluted fractions were introduced to analytical RP-HPLC to assess the purity of LPEI-PEG-EGFR tri-conjugate, fractions with 95% purity and higher were combined and were kept at −80° C. The concentration of the tri-conjugate was determined by copper assay. The amount of conjugated protein was determined by $A_{280}$ using Nano-Drop 2000.

Example 9

Anti-tumor Activity of PEI-PEG-EGFR Affibody

Figure 12A:
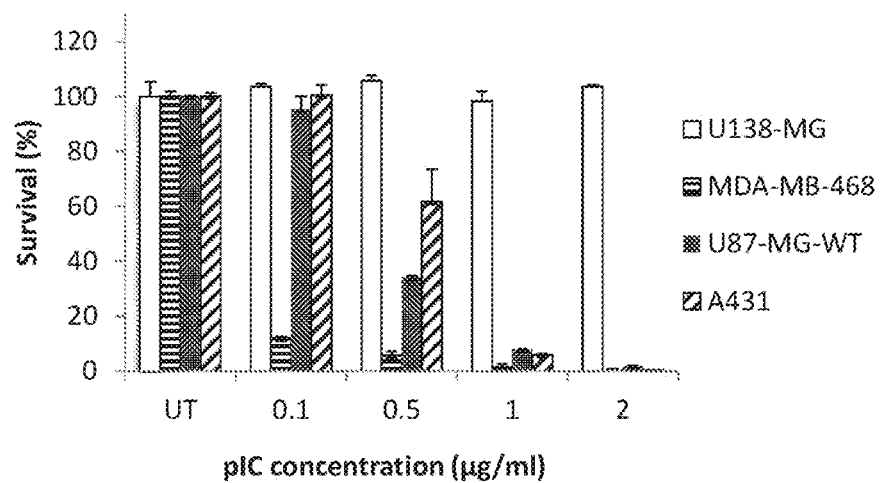
FIGS. 12A-B shows the efficacy of (A) PEI-PEG-EGF-RAffibody (PPEAffibody) in comparison to that of (B) PPE.
Figure 12B:
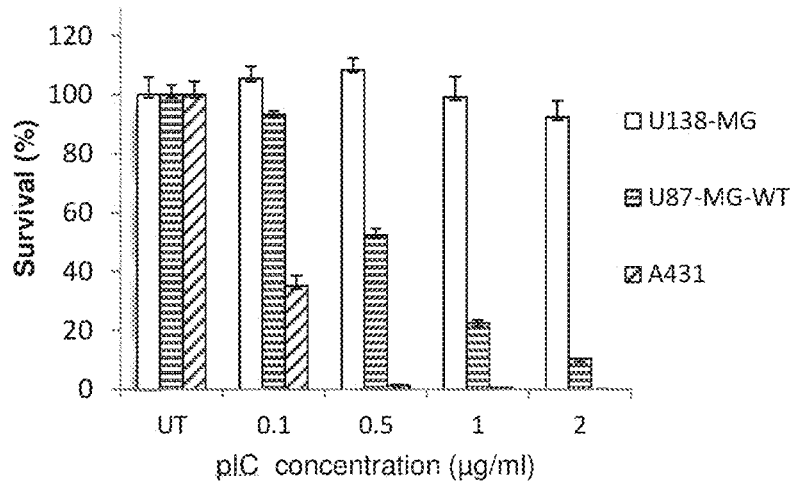

The PEI-PEG-EGFRAffibody (PPEA) complexed with PolyIC has strong anti-tumor activity. A variety cell lines overexpressing EGFR were found to be strongly inhibited by a complex of PEI-PEG-EGFRAffibody (PPEA) in complex with PolyInosine/PolyCytosine (PolyIC). It can be seen that the efficacy of PPEA is higher than that of PPE (FIG. 12).

The complex PolyIC/PPEA was found to possess strong anti-tumor activity in mouse models in which these cell lines were implanted in nude mice.

Figure 13:
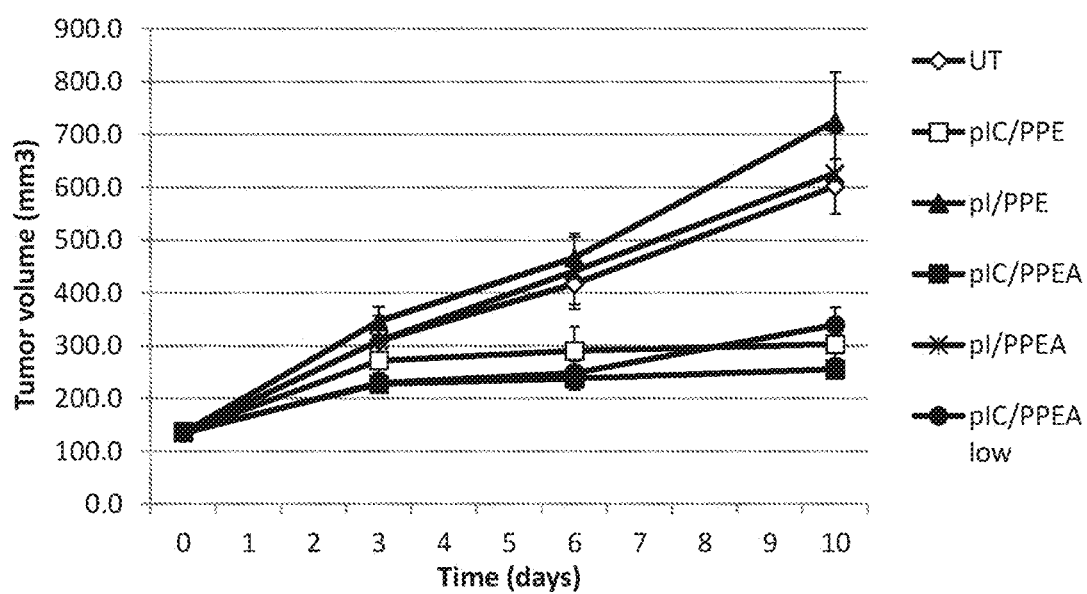
FIG. 13 shows the activity of PolyIC/PPEaffibody in vivo as compared with untreated (UT), pIC/PPE, pI/PPE, pI/PPEA and pIC/PPEA low (0.1 μ/μl pIC in the complex).

Sixty five female nude mice 5 weeks old were injected s.c. with 2 million $A_{431}$ cells. Seven days later tumors of average volume of 136 mm$^3$ had grown and mice were divided into 6 groups (7-8 mice/group) as follows: UT; pIC/PPEA, 0.75 mg/kg=250 µl of pIC for 25 gr mouse., IC, 6/week; pI/PPEA, 0.75 mg/kg IV, 6/week; pIC/PPEA low, 0.1 mg/kg=250 µl of 0.01 µg/µl pf pIC for 25 gr mouse IC, 6/week. pIC, pI and PPE and PPEA were diluted before mixing to obtain lower than ususal (0.1 µg/µl) concentration of pIC in the complex. FIG. 13 shows the activity of PolyIC/PPEffibody in vivo. Again, the efficacy of PPEA/PolyIC is higher than that of PolyIC/PPE.

Example 10

Synthesis of LPEI-PEG-h/mEGF 10.1. Synthesis of LPEI-PEG-SH Intermediate

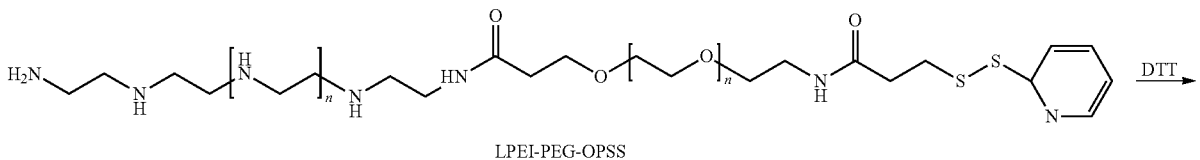

LPEI-PEG-OPSS

LPEI-PEG-SH

To 5 mg of LPEI-PEG-OPSS (0.2 mol, according to 24000 g/mol) in 5 ml of 20 mM HEPES (pH 7.4) buffer was added 50-fold molar excess of dithiothreitol (DTT; 0.1 mmol, 1.5 mg) and mixed by vortex for 20 min at room temperature in 15 ml plastic centrifugation tube. The reduced diconjugate was separated on Sephadex G-25 column (20 ml, 4×5 ml) using 5 ml sample loop and the elution performed with 20 mM HEPES, pH 7.4 at 1.0 ml/min flow rate and were analyzed by HPLC using the same conditions and method as described above.

Ellman's assay was used to evaluate the sulfhydryl group concentration in the LPEI-PEG-SH intermediate. The concentration of SH groups is directly proportional to the concentration of chromophor 6-nitro-3-thioxocyclohexa-1,4-diene-1-carboxylic acid, released by free thiols that react quantitatively with Ellman's reagent. The chromophor was measured via absorbance at 412 nm, without any interference from the sample or the Ellman's reagent.

10.2 Synthesis of m/hEGF-MCC Intermediate

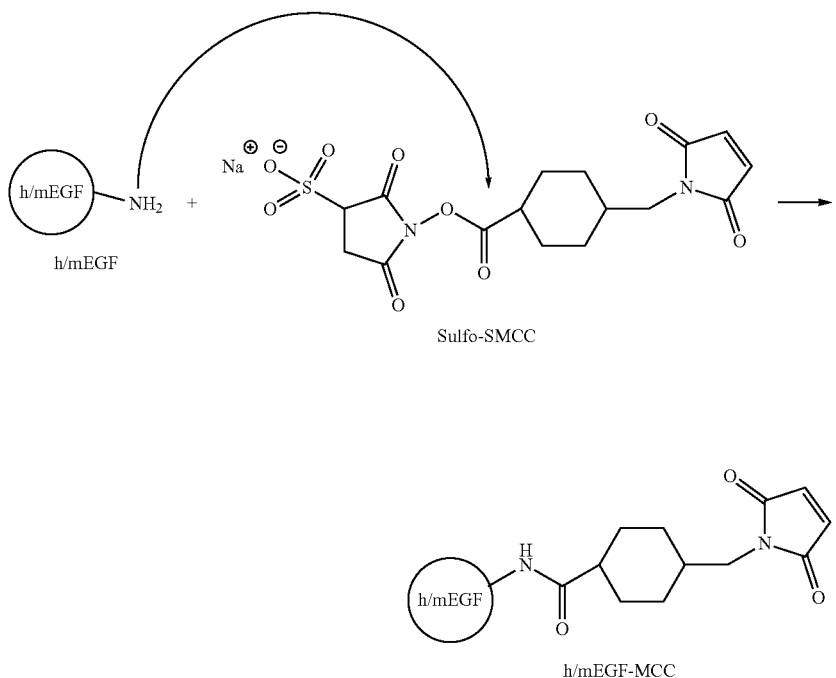

Synthesis outline. The h/mEGF (human/mouse Epidermal Growth Factor) was modified into h/mEGF-MCC (EGF-4-(N-Maleimidomethyl)cyclohexane-1-carboxylic acid; MCC) and purified to be later used for the conjugation with the LPEI-PEG-SH. Activating h/mEGF by attaching the MCC group circumvents reduction of the protein by DTT and allows to avoid exposure of h/mEGF to harsh conditions. This way the conjugation reaction efficiency is improved, moreover—EGF-MCC is a stable material that can be stored at −80° C. for weeks.

Synthesis of hEGF-MCC: 1 mg of hEGF (160 nmol) was reconstituted in 0.5 ml water then degassed with argon. The amount of hEGF was determined at 280 nm using nano-drop 2000. The solution was added to 0.5 ml of 200 mM sodium acetate buffer pH 6.0, and 60% ethanol while mixing vigorously. The solution was mixed with 10 equivalents of 4-(N-maleimidomethyl)cyclohexane-1-carboxylic acid 3-sulfo-N-hydroxysuccinimide ester sodium salt (Sulfo-SMCC) in 0.5 ml of 100% ethanol under argon. The slightly acidic pH of the reaction mixture (pH 6) was necessary to selectively modify the N-terminal amino group of hEGF. After 4 h at room temperature, the functionalized peptide was purified by dialysis bags (3.5k cutoff) against HBS (100 mM), three times in 1 L for 1 hour, then 1 L for overnight. The hEGF-MCC was analyzed using HPLC-mass spectra (MS) and had a molecular weight of 6435.7 g/mol, which indicates there is one conjugation of sulfo-SMCC to the hEGF. The HPLC-MS analysis was performed using Thermo SCIENTIFIC/ LCQ FLEET, equipped with reverse phase C-18 column (phenomenex, Aeris, 3.6 μm, 2.1 mm×50 mm, 100 A°).

Synthesis of mEGF-MCC: 0.5 mg (0.088 μmol total amount) of Murine EGF (PeproTech) was dissolved in 2100 μL of 20 mM HEPES buffer forming a clear viscous solution. One mg of sulfo-SMCC (30 eq., Ornat, Ill.) was dissolved in 0.9 mL absolute EtOH and slowly mixed with EGF solution to reach the final concentration of 30% EtOH in total 3.0 ml volume. Brief mixing resulted in a clear solution. The reaction vessel was shaken at ambient temperature for 4 hours. After that period of time the solution remained clear. The mEGF-MCC was first separated on Sephadex G-25 column (4×5 ml) and the elution performed with 20 mM HEPES, pH 7.4 at 1.0 ml/min flow rate and further purified and analyzed by HPLC using the same conditions and standard method as described above for LPEI-PEG-OPSS.

10.3 Synthesis of LPEI-PEG-h/mEGF

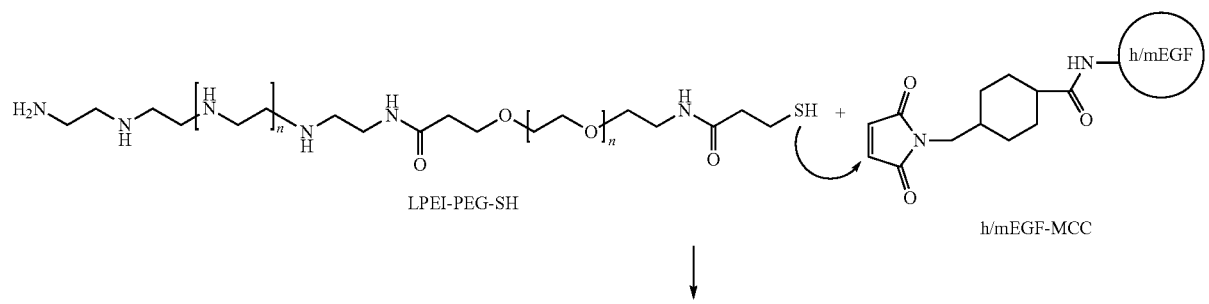

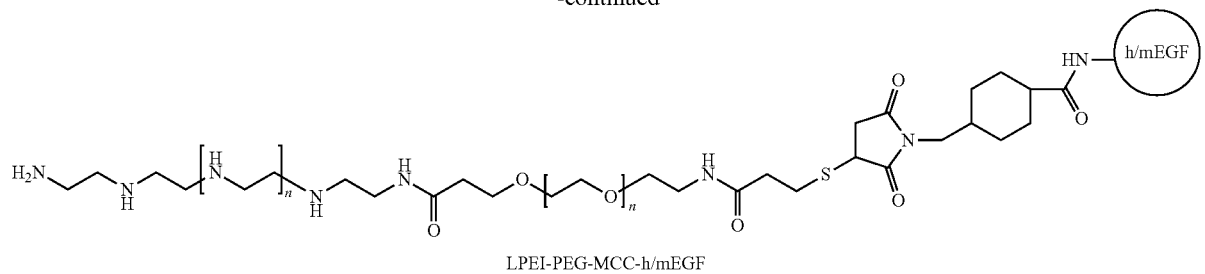

LPEI-PEG-MCC-h/mEGF

One and a half of equivalents of hEGF-MCC or mEGF-MCC were mixed with 1.0 equivalent of LPEI-PEG-SH. The reaction mixture was initially agitated at room temperature for 2 hours, and then incubated for 4 days at +4° C. with slow shaking. The reaction product (LPEI-PEG-hEGF or LPEI-PEG-mEGF) was separated by cation-exchange chromatography (7.8 cm MacroPrep High S resin (BioRad) in 10/1 cm Tricorn GE Healthcare column) using the gradient pump via A18 buffer inlet, at 0.5 ml/min flow rate and using solvent A: 20 mM HEPES pH 7.4 and solvent B: 20 mM HEPES pH 7.4 NaCl 3.0 M. The purified LPEI-PEG-hEGF or LPEI-PEG-mEGF triconjugate was analyzed by HPLC and quantified by a "copper assay" and an EGF photometric assay to measure [LPEI] and [EGF] concentrations, correspondingly.

10.4 Biological Activity of LPEI-PEG-hEGF.

Figure 14:
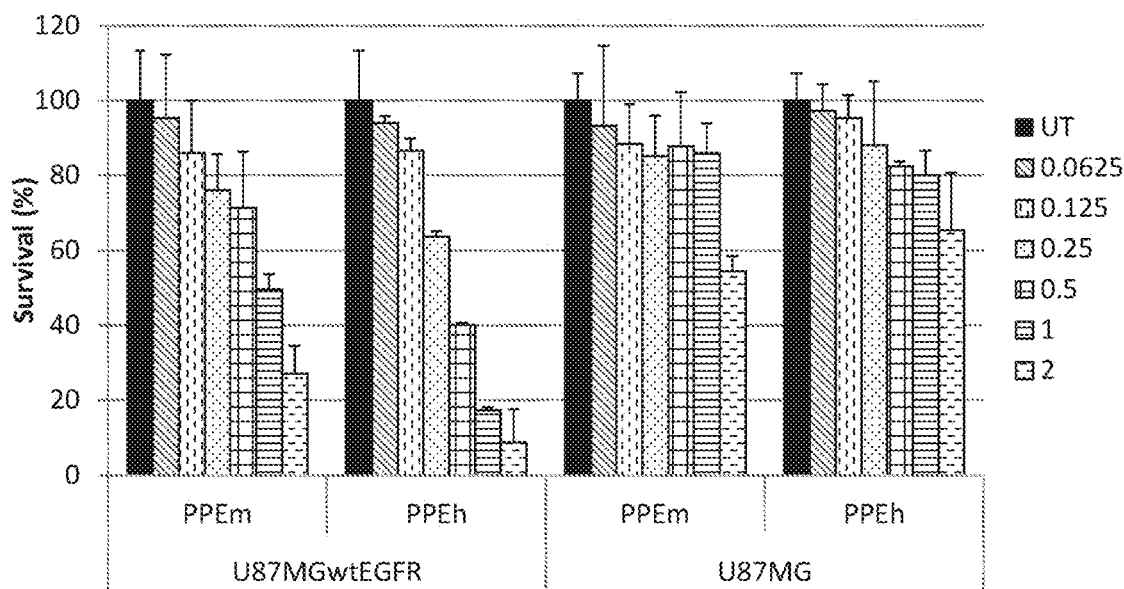
FIG. 14 shows survival of U87MG, U87MGwtEGFR cells after application of different concentrations of PolyIC/LPEI-PEG-hEGF complex as compared with application of PolyIC/mPPE (mouse) as described in Schaffert D, Kiss M, Rödl W, Shir A, Levitzki A, Ogris M, Wagner E. (2011) Poly(I:C)-mediated tumor growth suppression in EGF-receptor overexpressing tumors using EGF-polyethylene glycol-linear polyethylenimine as carrier. Pharm Res. 28:731-41.

Using the cellular assay we usually employ we compared the activity of the PolyIC/LPEI-PEG-hEGF complex (PPEm) with the PolyIC/mPPE (mouse) described in Schaffert D, Kiss M, Rödl W, Shir A, Levitzki A, Ogris M, Wagner E., 2011 (Poly(I:C)-mediated tumor growth suppression in EGF-receptor overexpressing tumors using EGF-polyethylene glycol-linear polyethylenimine as carrier. Pharm Res. 28:731-41). It can be seen that the new HEGF conjugate is more effective in killing EGFR over-expressing cells (FIG. 14). Cells that express moderate amounts of EGFR molecules on their surface (U87MG cells express 80,000 EGFRs/cell) are less sensitive to the treatment than cells over-expressing massive amounts (U87MGwtEGFR cells express 1,000,000 EGFRs/cell).

Example 11

Synthesis of DUPA Analog-DyLight 680

The peptide was synthesized using standard Fmoc solid-phase peptide synthesis (SPPS) procedures on Fmoc-Cys(trt) wang resin as the solid support. Swelling: the resin was swelled for at least 2 h in dichloromethane. Fmoc removal: the resin was first treated with a solution of 20% piperidine in dimethylformamide (DMF) (2×20 min), then washed with DMF (5×2 min). Coupling of Fmoc-Asp(OtBu)—OH: 3 eq. of Fmoc-Asp(OtBu)-OH, 3 eq. of (1-[bis(dimethylamino)methylene]-1H-1,2,3-triazolo [4,5-b]pyridinium 3-oxid hexafluorophosphate) (HATU) were dissolved in 15 ml of DMF and 8 eq. of N,N-diisopropylethylamine (DIEA or DIPEA) were added to the mixture. The solution was mixed (pre-activated) for 10 minutes at room temperature before it was added to the resin for 1 hour. The coupling was repeated twice with the new mixture in order to ensure complete coupling of aspartic acid. A Keiser test was performed to ensure a complete coupling. The resin was washed with DMF (3×2 minutes) and dichloromethane (DCM) (2×2 min). Capping: The resin was treated with a solution of acetic anhydride (10 eq.) and DIPEA (8 eq.) in DMF for 20 min and washed with DMF (3×2 min). Fmoc removal.: The resin was first treated with a solution of 20% piperidine in DMF (2×20 min), then washed with DMF (5×2 min). Coupling of Fmoc-diaminopropionic(DAP) acid: 3 eq. of Fmoc-diaminopropionic (DAP) acid, 3 eq. of HATU and 8 eq. of DIEA were dissolved in 15 ml of DMF. The solution was mixed (pre-activated) for 10 minutes at room temperature before it was added to the resin for 1 hour. A Keiser test was performed to ensure a complete coupling. The resin was washed with DMF (3×2 minutes) and DCM (2×2 min). Peptide elongation: the following compounds were coupled to the resin in the following order (1) Fmoc-Phe-OH, (2) Fmoc-Phe-OH, (3) Fmoc-8-aminooctanoic (EAO) acid, and (4) OtBu-Glu(Fmoc)-OH. Fmoc removal: the resin was treated with a solution of 20% piperidine in DMF (2×20 min), then washed with DMF (5×2 min) and DCM (3×2 min). Coupling of the DUPA ligand: 0.9 mL of triethylamine (6.6 mmol) was combined with 0.9 gr (3 mmol) of L-glutamic acid di-tertbutyl ester hydrochloride in 15 mL DCM. This solution was added dropwise over 45 minutes to a solution of 5 mL DCM and triphosgene (0.35 g, 1.1 mmol) at 0° C. After stirring for additional 50 min the mixture was added to the resin with additional 0.9 mL of triethylamine. The reaction mixture with the resin was shaked for 3 hours and washed with DMF (3×2 min). Full Cleavage: the resin was washed with DCM (3×2 min) and dried under vacuum. A solution of 2.5% TDW and 2.5% triisopropylsilane in trifluoroacetic acid (TFA) at 0° C. was added. The reaction proceeded for 4 h at room temperature, filtered and treated with a cooled solution of ether/hexane 1:1, and the peptides were precipitated by centrifugation. The crude peptides were dissolved in acetonitrile/TDW 1:1 solution and lyophilized. The crude was purified by preparative reverse phase (RP) HPLC. DyLight 680 Coupling: under argon atmosphere, 1 mg of DyLight™ 680 (Life Technologies, Cat. No. 46418) was dissolved in anhydrous dimethyl sulfoxide (DMSO; 100 μL) containing 50 equivalents of anhydrous diisopropylethylamine. A two-fold molar excess of a DUPA peptide linker dissolved in anhydrous DMSO (100 μL) was added to the above mixture and stirred at room temperature. The formations of products were confirmed by liquid chromatography-mass spectrometry (LC-MS). The crude DUPA near-infrared (NIR) probes were then purified by preparative RP-HPLC.

Example 12

Synthesis of Dupa analog-Drug Lead

The peptide was synthesized using standard Fmoc SPPS procedures on Fmoc-Cys(trt) wang resin as the solid support. Swelling: the resin was swelled for at least 2 h in dichloromethane. Fmoc removal: the resin was treated with a solution of 20% piperidine in DMF (2×20 min), then washed with DMF (5×2 min). Coupling of Fmoc-Gly-OH: 3 eq. of Fmoc-Gly-OH, and 3 eq. of HATU were dissolved in 15 ml of DMF, followed by addition of 8 eq. of DIEA. The solution was mixed (pre-activated) for 10 minutes at room temperature before it was added to the resin for 1 hour. The coupling was repeated twice with the new mixture. A Keiser test was performed to ensure a complete coupling. The resin was washed with DMF (3×2 minutes) and DCM (2×2 min). Capping: The resin was treated with a solution of acetic anhydride (10 eq.) and DIPEA (8 eq.) in DMF for 20 min and washed with DMF (3×2 min). Fmoc removal: the resin was treated with a solution of 20% piperidine in DMF (2×20 min), then washed with DMF (5×2 min). Coupling of Fmoc-Trp(Boc)-OH: 3 eq. of the Fmoc-Trp(Boc)-OH, 3 eq. of HATU and 8 eq. of DIEA were dissolved in 15 ml DMF. The solution was mixed (pre-activated) for 10 minutes at room temperature before it was added to the resin for 1 hour. A Keiser test was performed to ensure a complete coupling. The resin was washed with DMF (3×2 min) and DCM (2×2 min). Peptide elongation: the following compounds were coupled to the resin in the following order (1) Fmoc-Trp (Boc)-OH, (2) Fmoc-Gly-OH, (3) Fmoc-Phe-OH, (4) Fmoc-8-aminooctanoic(EAO) acid, and (5) OtBu-Glu(Fmoc)-OH. Fmoc removal: the resin was treated with a solution of 20% piperidine in DMF (2×20 min), then washed with DMF (5×2 min) and DCM (3×2 min). Coupling of the DUPA ligand: 0.9 mL of triethylamine (6.6 mmol) was combined with 0.9 gr (3 mmol) of L-glutamic acid di-terlbutyl ester hydrochloride in 15 mL DCM. This solution was added dropwise over 45 minutes to a solution of 5 mL DCM and triphosgene (0.35 g, 1.1 mmol) at 0° C. After stirring for additional 50 min the mixture was added to the resin with additional 0.9 mL of triethylamine. The reaction mixture with the resin was shaked for 3 hours and washed with DMF (3×2 min). Full Cleavage: the resin was washed with DCM (3×2 min) and dried under vacuum. A solution of 2.5% TDW and 2.5% triisopropylsilane in trifluoroacetic acid (TFA) at 0° C. was added. The reaction proceeded for 4 h at room temperature, filtered and treated with a cooled solution of ether/hexane 1:1, and the peptides containing the DUPA analog were precipitated by centrifugation. The crude peptides were dissolved in acetonitrile/TDW 1:1 solution and lyophilized. The crude was purified by preparative RP-HPLC. Synthesis of PEI-PEG-DUPA analog: 4.37 mg (1.2×10$^4$ mmol) of di-conjugate 1:1 or 1:3 (prepared as explained in Example 1 herein above) were dissolved in 940 µl of 20 mM HEPES pH 7.4. Then, 1 mg (9.1×10$^{-4}$ mmol, ~5 eq) of the DUPA analog, was dissolved in 2 ml of acetonitrile (ACN; HPLC grade)/(20 mM HEPES pH 7.4) at a ratio of 1:1, were added dropwise to the reaction. Then, to reach an approximate ~10% total concentration of ACN in the reaction, an addition of 4 mL of 20 mM were introduced into the reaction mixture. The reaction was further vortexed (800 rpm) in the dark at room temperature until the absorption at wavelength 343 ($A_{343}$) indicated a complete turnover. The resulting tri-conjugate was purified by cation exchange chromatography on a HR10/10 column filled with MacroPrep High S resin (BioRad) (using a three-step gradient elution of 20 mM HEPES pH 7.4 to 20 mM HEPES containing 3 M NaCl). The eluted fractions were introduced to an analytical RP-HPLC to assess the purity of the tri-conjugate. Fractions with 95% purity and higher were combined and were kept at −80° C. The concentration of the tri-conjugate was determined by the copper assay. The amount of conjugated DUPA analog was determined by the chromophores' (Trp amino acid) absorption.

Example 13

PolyIC/LPEI-PEG-DUPA Targets Prostate Cancer

Prostate surface membrane antigen (PSMA) is overexpressed in metastatic prostate cancer. It is also found in the neovasculature of most solid tumors. Since PSMA is internalized upon ligand binding we have chosen it as a target, design and synthesize a PolyIC PSMA targeting vector. Indeed, DUPA-Daylight680 is internalized to PSMA overexpressing cells (LNCaP) but not to MCF7 (overexpressing Her2) (not shown).

Figure 15:
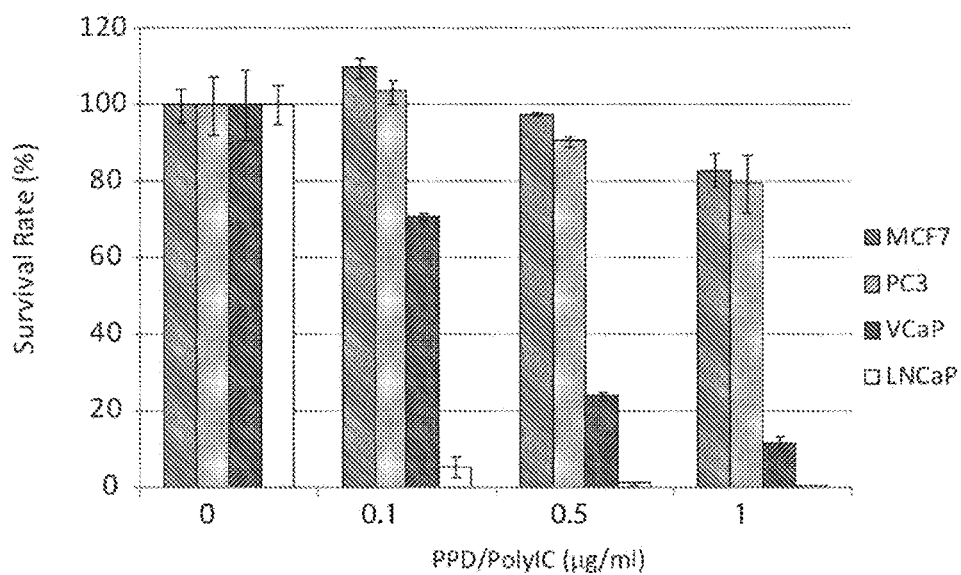
FIG. 15 shows that PEI-PEG (PP)-DUPA (PPD)/PolyIC is highly effective against LNCaP and VCaP cells. Viability was measured after 96 hr of exposure.
Figure 16A:
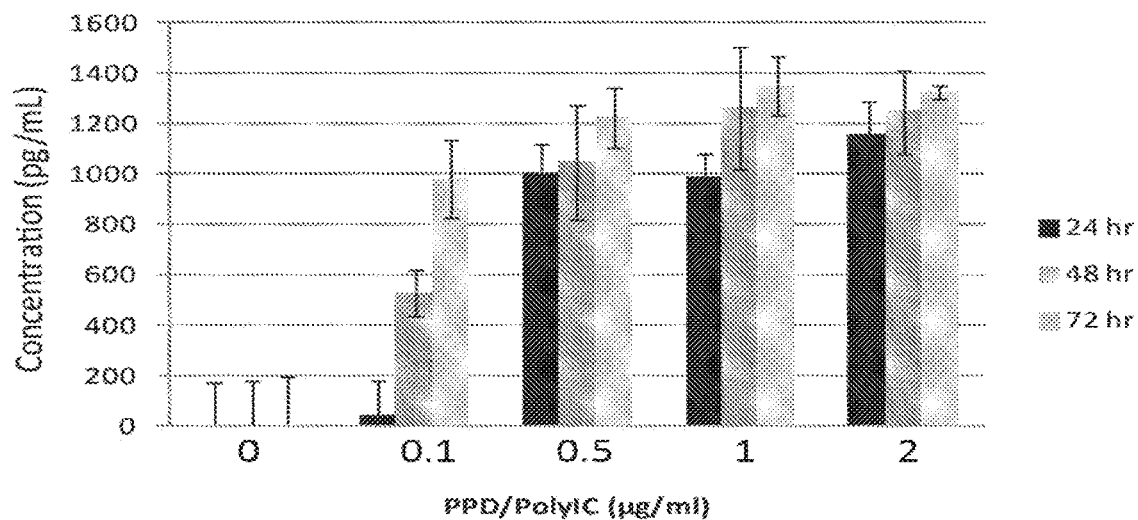
FIGS. 16A-B shows production of the cytokines (A) IP-10, (B) Gro-α by LNCaP cell transfected with PolyIC/PPD.
Figure 16B:
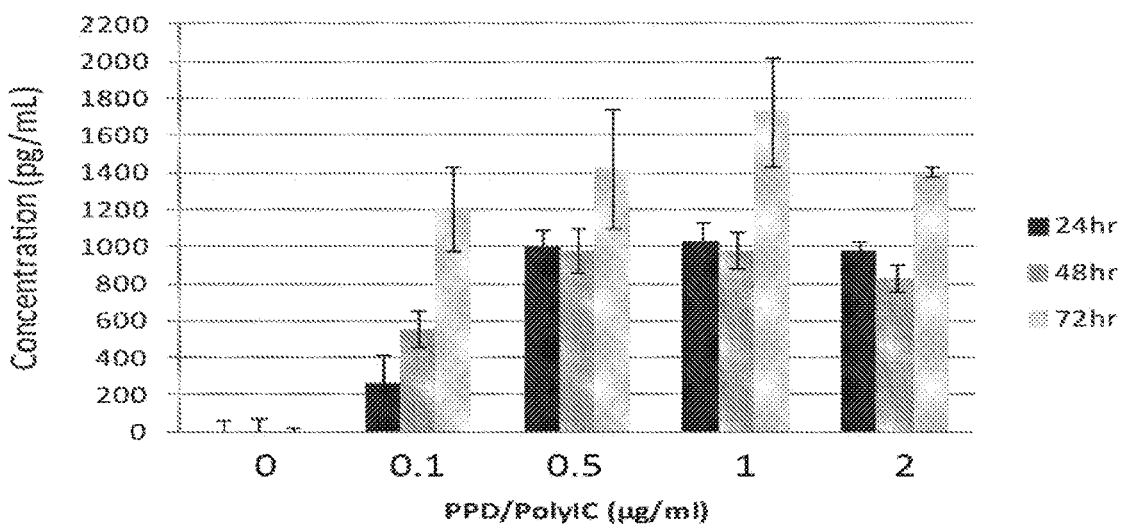
Figure 17:
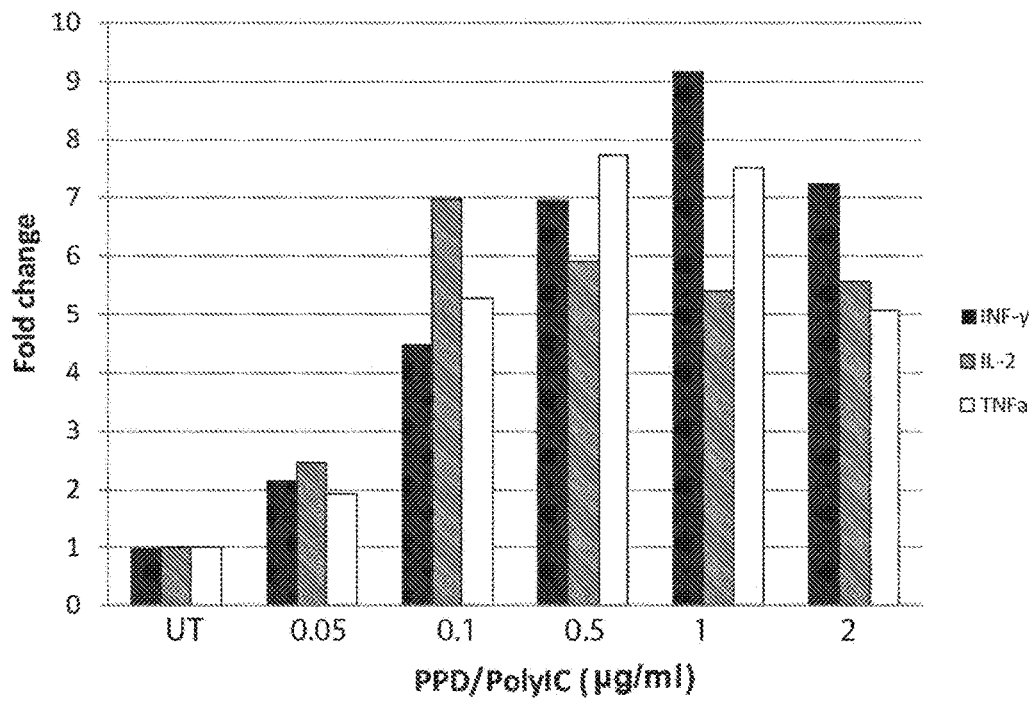
FIG. 17 shows that medium conditioned by LNCaP cells stimulates expression of cytokines INF-γ, IL-2 and TNF-α in PBMCs grown in the conditioned medium.
Figure 18:
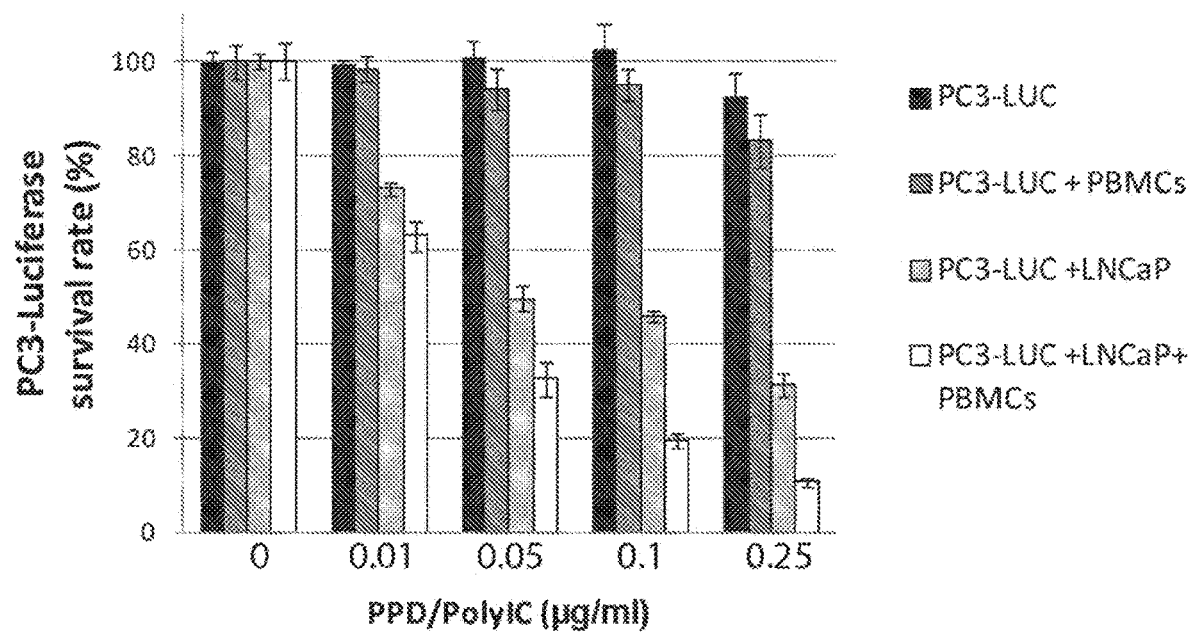
FIG. 18 shows that co-incubation of PolyIC/PPD treated LNCaP cells with PC3-Luciferase cells which do not express PSMA, resulted in up to 70% killing of the PC3-Luciferase cells via bystander effect. Addition of healthy human PBMCs strongly enhanced the effect and lead to the killing of 90% of the PC3 cells.

FIG. 15 shows that PEI-PEG-DUPA (PPD)/PolyIC is highly effective against LNCaP and VCaP cells. Viability was measured after 96 hr of exposure. PPD also induces the production of cytokines (FIG. 16). In FIG. 17, it is demonstrated that medium conditioned by LNCaP cells stimulates expression of the cytokines INF-γ, IL-2 and TNF-α in PBMCs grown in the conditioned medium. It was then shown that co-incubation of PolyIC/PPD treated LNCaP cells with PC3-Luciferase cells which do not express PSMA, resulted in up to 70% killing of the PC3-Luciferase cells via bystander effect. Addition of healthy human PBMCs strongly enhanced the effect and lead to the killing of 90% of the PC3 cells (FIG. 18).

Example 14

Cancer Treatment In Vivo

Figure 19:
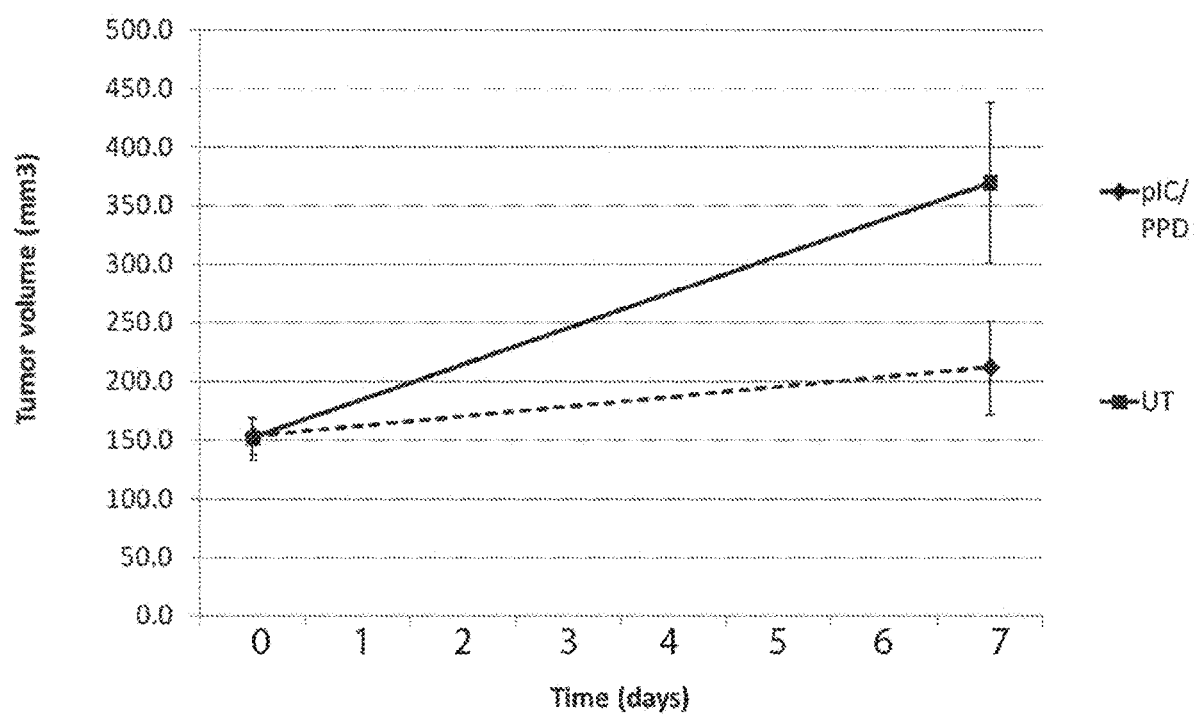
FIG. 19 shows effect of PolyIC/PPD on subcutaneous LNCaP tumors in vivo. UT, untreated.

PolyIC/PPD has significant anti-tumor effects when tested in SCID mice (FIG. 19). Tumor inhibition is not complete due to the lack of immune system in the experimental mice.

REFERENCES

1. Boussif, O., et al., A versatile vector for gene and oligonucleotide transfer into cells in culture and in vivo: polyethylenimine. Proc Natl Acad Sci U S A, 1995. 92(16): p. 7297-301.
2. Wagner, E., et al., Transferrin-polycation-DNA complexes: the effect of polycations on the structure of the complex and DNA delivery to cells. Proc Natl Acad Sci U S A, 1991. 88(10): p. 4255-9.
3. Little, S. R., et al., Poly-beta amino ester-containing microparticles enhance the activity of nonviral genetic vaccines. Proc Natl Acad Sci U S A, 2004. 101(26): p. 9534-9.
4. Davis, M. E., Z. G. Chen, and D. M. Shin, Nanoparticle therapeutics: an emerging treatment modality for cancer. Nat Rev Drug Discov, 2008. 7(9): p. 771-82.
5. Remy, J. S., et al., Targeted gene transfer into hepatoma cells with lipopolyamine-condensed DNA particles presenting galactose ligands: a stage toward artificial viruses. Proc Natl Acad Sci U S A, 1995. 92(5): p. 1744-8.
6. Jager, M., et al., Branched and linear poly(ethylene imine)-based conjugates: synthetic modification, characterization, and application. Chem Soc Rev, 2012. 41(13): p. 4755-67.
7. Ziebarth, J. D. and Y. Wang, Understanding the protonation behavior of linear polyethylenimine in solutions through Monte Carlo simulations. Biomacromolecules, 2010. 11(1): p. 29-38.

8. Hobel, S., et al., Maltose- and maltotriose-modified, hyperbranched poly(ethylene imine)s (OM-PEIs): Physicochemical and biological properties of DNA and siRNA complexes. J Control Release, 2011. 149(2): p. 146-58.

9. Rejman, J., A. Bragonzi, and M. Conese, Role of clathrin- and caveolae-mediated endocytosis in gene transfer mediated by lipo- and polyplexes. Mol Ther, 2005. 12(3): p. 468-74.

10. Behr, J. P., The proton sponge: A trick to enter cells the viruses did not exploit. Chimia, 1997. 51(1-2): p. 34-36.

11. Suh, J., H. J. Paik, and B. K. Hwang, Ionization of Poly(Ethylenimine) and Poly(Allylamine) at Various Phs. Bioorganic Chemistry, 1994. 22(3): p. 318-327.

12. Ogris, M., et al., PEGylated DNA/transferrin-PEI complexes: reduced interaction with blood components, extended circulation in blood and potential for systemic gene delivery. Gene Ther, 1999. 6(4): p. 595-605.

13. Schaffert, D., et al., Poly(I:C)-mediated tumor growth suppression in EGF-receptor overexpressing tumors using EGF-polyethylene glycol-linear polyethylenimine as carrier. Pharm Res, 2011. 28(4): p. 731-41.

14. Nilsson, B., et al., A synthetic IgG-binding domain based on staphylococcal protein A. Protein Eng, 1987. 1(2): p. 107-13.

15. Lofblom, J., et al., Affibody molecules: engineered proteins for therapeutic, diagnostic and biotechnological applications. FEBS Lett, 2010. 584(12): p. 2670-80.

16. Brissault, B., et al., Synthesis, characterization, and gene transfer application of poly(ethylene glycol-b-ethylenimine) with high molar mass polyamine block. Biomacromolecules, 2006. 7(10): p. 2863-70.

17. Ungaro, F., et al., Spectrophotometric determination of polyethylenimine in the presence of an oligonucleotide for the characterization of controlled release formulations. J Pharm Biomed Anal, 2003. 31(1): p. 143-9.

18. Gebhart, C. L., et al., Design and formulation of polyplexes based on pluronic-polyethyleneimine conjugates for gene transfer. Bioconjug Chem, 2002. 13(5): p. 937-44.

19. Dent, M. F., et al., The methylene blue colorimetric microassay for determining cell line response to growth factors. Cytotechnology, 1995. 17(1): p. 27-33.

20. Eigenbrot, C., et al., Structural basis for high-affinity HER2 receptor binding by an engineered protein. Proc Natl Acad Sci U S A, 2010. 107(34): p. 15039-44.

21. Ogris, M., et al., The size of DNA/transferrin-PEI complexes is an important factor for gene expression in cultured cells. Gene Ther, 1998. 5(10): p. 1425-33.

22. Chollet, P., et al., Side-effects of a systemic injection of linear polyethylenimine-DNA complexes. J Gene Med, 2002. 4(1): p. 84-91.

23. Champion, J. A., Y. K. Katare, and S. Mitragotri, Particle shape: A new design parameter for micro- and nanoscale drug delivery carriers. Journal of Controlled Release, 2007. 121(1-2): p. 3-9.

24. Kleemann, E., et al., Nano-carriers for DNA delivery to the lung based upon a TAT-derived peptide covalently coupled to PEG-PEI. J Control Release, 2005. 109(1-3): p. 299-316.

25. Rudolph, C., et al., Nonviral gene delivery to the lung with copolymer-protected and transferrin-modified polyethylenimine. Biochim Biophys Acta, 2002. 1573(1): p. 75-83.

26. Aguilar, Z., et al., Biologic effects of heregulin/neu differentiation factor on normal and malignant human breast and ovarian epithelial cells. Oncogene, 1999. 18(44): p. 6050-62.

27. Park, J. W., et al., Anti-HER2 immunoliposomes: enhanced efficacy attributable to targeted delivery. Clin Cancer Res, 2002. 8(4): p. 1172-81.

28. Rabenstein, D. L., Heparin and heparan sulfate: structure and function. Nat Prod Rep, 2002. 19(3): p. 312-31.

29. Seib, F. P., A. T. Jones, and R. Duncan, Comparison of the endocytic properties of linear and branched PEIs, and cationic PAMAM dendrimers in B16f10 melanoma cells. J Control Release, 2007. 117(3): p. 291-300.

30. Jeong, G. J., et al., Biodistribution and tissue expression kinetics of plasmid DNA complexed with polyethylenimines of different molecular weight and structure. J Control Release, 2007. 118(1): p. 118-25.

31. Kawakami, S., et al., Evaluation of proinflammatory cytokine production induced by linear and branched polyethylenimine/plasmid DNA complexes in mice. J Pharmacol Exp Ther, 2006. 317(3): p. 1382-90.

32. Goula, D., et al., Polyethylenimine-based intravenous delivery of transgenes to mouse lung. Gene Ther, 1998. 5(9): p. 1291-5.

33. Bragonzi, A., et al., Comparison between cationic polymers and lipids in mediating systemic gene delivery to the lungs. Gene Ther, 1999. 6(12): p. 1995-2004.

34. Lee, K., et al., Pluronic/polyethylenimine shell crosslinked nanocapsules with embedded magnetite nanocrystals for magnetically triggered delivery of siRNA. Macromol Biosci, 2010. 10(3): p. 239-45.

35. Zheng, M., et al., Poly(ethylene oxide) grafted with short polyethylenimine gives DNA polyplexes with superior colloidal stability, low cytotoxicity, and potent in vitro gene transfection under serum conditions. Biomacromolecules, 2012. 13(3): p. 881-8.

36. Petersen, H., et al., Polyethylenimine-graft-poly(ethylene glycol) copolymers: influence of copolymer block structure on DNA complexation and biological activities as gene delivery system. Bioconjug Chem, 2002. 13(4): p. 845-54.

37. Champion, J. A., Y. K. Katare, and S. Mitragotri, Particle shape: a new design parameter for micro- and nanoscale drug delivery carriers. J Control Release, 2007. 121(1-2): p. 3-9.

38. Liu, Y., et al., The shape of things to come: importance of design in nanotechnology for drug delivery. Ther Deliv, 2012. 3(2): p. 181-94.

39. Kloeckner, J., et al., Photochemically enhanced gene delivery of EGF receptor-targeted DNA polyplexes. J Drug Target, 2004. 12(4): p. 205-13.

40. Kircheis, R., et al., Polyethylenimine/DNA complexes shielded by transferrin target gene expression to tumors after systemic application. Gene Ther, 2001. 8(1): p. 28-40.

41. Ogris, M., et al., DNA/polyethylenimine transfection particles: influence of ligands, polymer size, and PEGylation on internalization and gene expression. AAPS PharmSci, 2001. 3(3): p. E21.

What is claimed is:

1. A polyplex of a double stranded RNA (dsRNA) and a polymeric conjugate, wherein the dsRNA is polyinosinic-polycytidylic acid double stranded RNA (poly I:C), wherein said polymeric conjugate consists of a linear polyethyleneimine (LPEI) covalently linked to one or more polyethylene glycol (PEG) moieties, each PEG moiety being conjugated via a linker to a targeting moiety capable of binding to a cancer antigen, wherein the polymeric conjugate is a diconjugate of the formula (i)-(viii), linked to said targeting moiety/moieties:

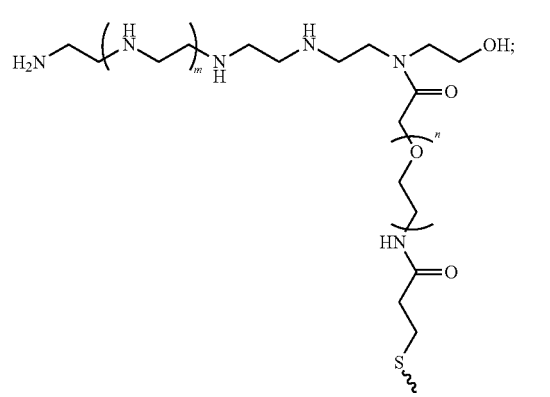
(i)

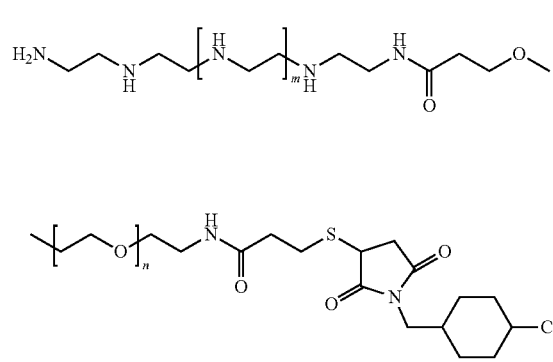
(ii)

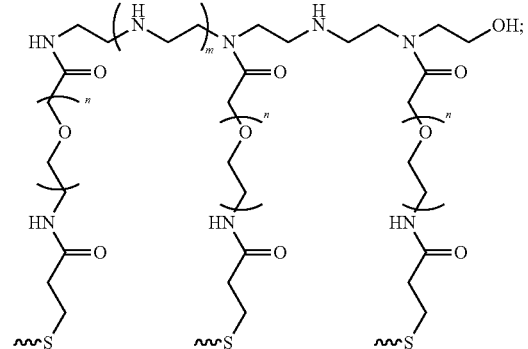
(iii)

—(NH—(CH$_2$)$_7$—CO)-Phe-Phe—(NH—CH$_2$—CH(NH$_2$)—
—CO)-Asp-Cys-PEG$_{2k}$-LPEI;
(iv)

—(NH—(CH$_2$)$_7$—CO)-Phe-Gly-Trp-Trp-Gly-Cys-PEG$_{2k}$-LPEI;
(v)

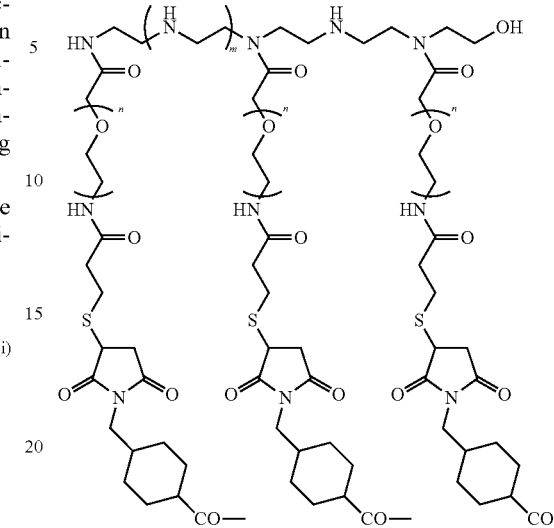
(vi)

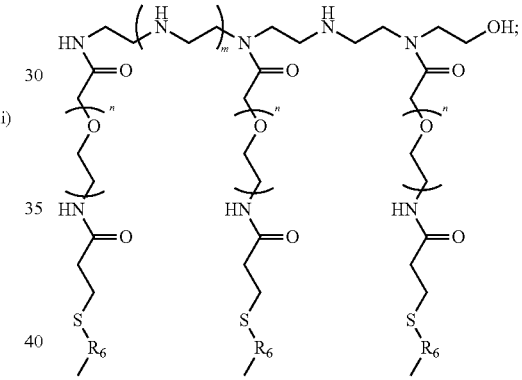
(vii)

wherein R$_6$ is

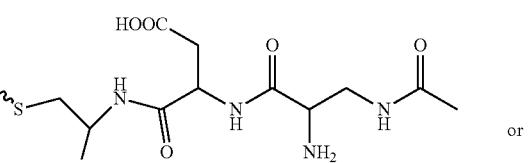 or

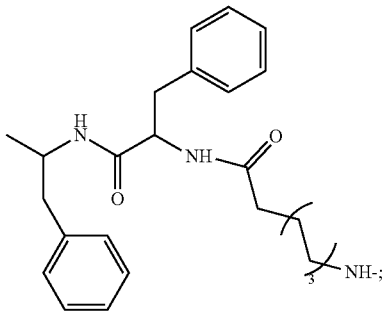

-continued

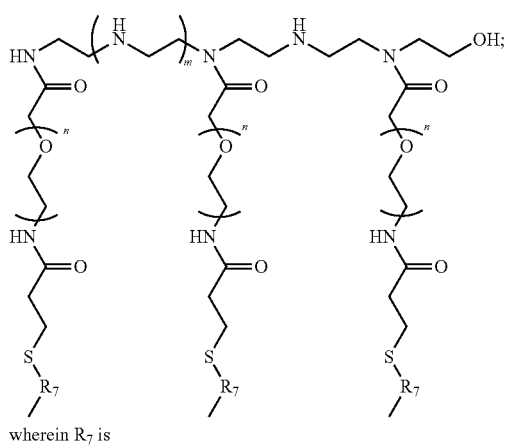

(viii)

wherein R₇ is

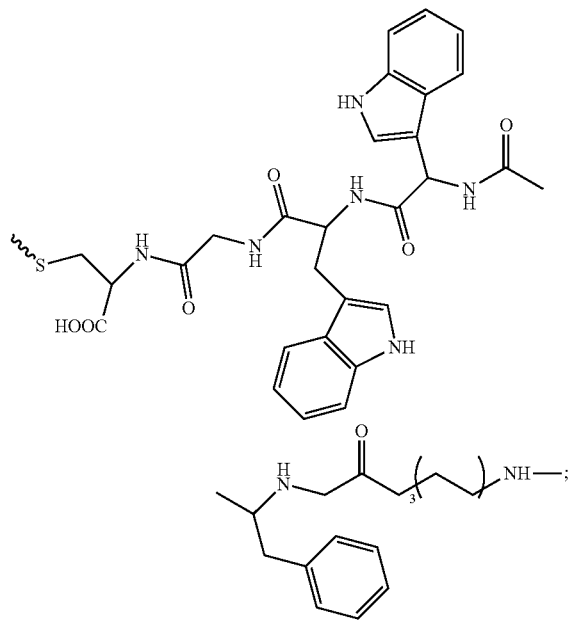

and
wherein m and n are ≥1.

2. The polyplex of claim 1, wherein m is 200-700 and n is 20-200.

3. The polyplex of claim 1, wherein each strand of said dsRNA has 20-300 ribonucleotides.

4. The polyplex of claim 1, wherein
(a) said targeting moiety is HER2 affibody, and said polymeric conjugate is of the formula (i) of claim 1, and the HER2 affibody is linked via a mercapto group thereof;
(b) said targeting moiety is HER2 affibody, and said polymeric conjugate is of the formula (v) of claim 1, and the HER2 affibody is linked via a mercapto group thereof;
(c) said targeting moiety is EGFR affibody, and said polymeric conjugate is of the formula (i) of claim 1, and the EGFR affibody is linked via a mercapto group thereof;
(d) said targeting moiety is EGFR affibody, and said polymeric conjugate is of the formula (v) of claim 1, and the EGFR affibody is linked via a mercapto group thereof;

(e) said targeting moiety is hEGF, and said polymeric conjugate is of the formula (ii) of claim 1, wherein the hEGF is linked via an amino group thereof;
(f) said targeting moiety is hEGF, and said polymeric conjugate is of the formula (vi) of claim 1, wherein the hEGF is linked via an amino group thereof;
(g) said targeting moiety is HOOC(CH₂)₂—CH(COOH)—NH—CO—NH—CH(COOH)—(CH₂)₂—CO— (DUPA residue), and said polymeric conjugate is of the formula (iii) of claim 1;
(h) said targeting moiety is HOOC(CH₂)₂—CH(COOH)—NH—CO—NH—CH(COOH)—(CH₂)₂—CO— (DUPA residue), and said polymeric conjugate is of the formula (vii) of claim 1;
(i) said targeting moiety is HOOC(CH₂)₂—CH(COOH)—NH—CO—NH—CH(COOH)—(CH₂)₂—CO— (DUPA residue), and said polymeric conjugate is of the formula (iv) of claim 1; or
(j) said targeting moiety is HOOC(CH₂)₂—CH(COOH)—NH—CO—NH—CH(COOH)—(CH₂)₂—CO— (DUPA residue), and said polymeric conjugate is of the formula (viii) of claim 1.

5. The polyplex of claim 1, wherein the cancer antigen is epidermal growth factor receptor (EGFR), human epidermal growth factor receptor 2 (HER2) or prostate surface membrane antigen (PSMA).

6. The polyplex of claim 5, wherein said targeting moiety is hEGF, and the hEGF is linked via an amino group thereof.

7. The polyplex of claim 6, wherein said polymeric conjugate is a diconjugate of the formula (ii) linked to said targeting moiety.

8. The polyplex of claim 6, wherein said polymeric conjugate is a diconjugate of the formula (vi) linked to said targeting moieties.

9. The polyplex of claim 7, wherein the cancer antigen is epidermal growth factor receptor (EGFR).

10. The polyplex of claim 1, wherein said polymeric conjugate is a diconjugate of the formula (iv) linked to said targeting moiety.

11. The polyplex of claim 10, wherein said targeting moiety is HOOC(CH2)2—CH(COOH)—NH—CO—NH—CH(COOH)—(CH₂)2—CO— (DUPA residue).

12. The polyplex of claim 11, wherein the cancer antigen is prostate surface membrane antigen (PSMA).

13. A polyplex of a double stranded RNA (dsRNA) and a polymeric conjugate, wherein the dsRNA is polyinosinic-polycytidylic acid double stranded RNA (poly I:C), wherein said polymeric conjugate consists of a linear polyethyleneimine (LPEI) covalently linked to one or more polyethylene glycol (PEG) moieties, each PEG moiety being conjugated via a linker to a targeting moiety capable of binding to a cancer antigen,
wherein said linker forms an —S—S—, NH—CO—, —CO—NH—, —S—C—, O—CO—, —CO—O— or urea (—NH—CO—NH) bond with said targeting moiety, and
wherein said linker is a peptide moiety; wherein said peptide moiety is —(NH—(CH₂)₇—CO)-Phe-Gly-Trp-Trp-Gly-Cys- (SEQ ID NO: 2) or —(NH—(CH₂)₇—CO)-Phe-Phe-(NH—CH₂—CH(NH₂)—CO)-Asp-Cys- (SEQ ID NO: 3).

14. The polyplex of claim 13, wherein each strand of said dsRNA has 20-300 ribonucleotides.

15. The polyplex of claim 13, wherein said peptide moiety is —(NH—(CH₂)₇—CO)-Phe-Gly-Trp-Trp-Gly-Cys- (SEQ ID NO: 2).

16. The polyplex of claim 15, wherein said linker forms an NH—CO— or —CO—NH— bond with said targeting moiety.

17. The polyplex of claim 16, wherein the polymeric conjugate consists of LPEI covalently linked to one PEG moiety.

18. The polyplex of claim 17, wherein the cancer antigen is prostate surface membrane antigen (PSMA).

19. A polyplex of a double stranded RNA (dsRNA) and a polymeric conjugate, wherein said polymeric conjugate consists of a linear polyethyleneimine (LPEI) covalently linked to one polyethylene glycol (PEG) moiety, said PEG moiety being conjugated via a linker to a targeting moiety capable of binding to a cancer antigen, wherein the polymeric conjugate is a diconjugate of the formula (ii) linked to said targeting moiety

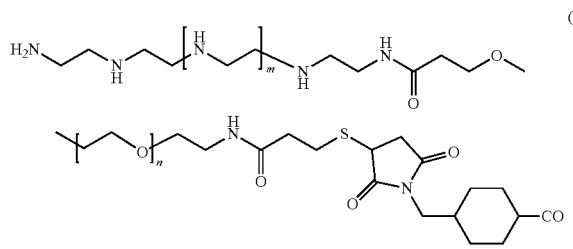

(ii)

and wherein said targeting moiety is hEGF, wherein the hEGF is linked via an amino group to said linker, and wherein said dsRNA is polyinosinic-polycytidylic acid double stranded RNA (poly I:C), and wherein m is 200-700 and n is 20-200.

20. A polyplex of a double stranded RNA (dsRNA) and a polymeric conjugate, wherein said polymeric conjugate consists of a linear polyethyleneimine (LPEI) covalently linked to one polyethylene glycol (PEG) moiety, said PEG moiety being conjugated via a linker to a targeting moiety capable of binding to a cancer antigen, wherein the polymeric conjugate is a diconjugate of the formula (iv) linked to said targeting moiety (iv) —(NH—(CH$_2$)$_7$—CO)-Phe-Gly-Trp-Trp-Gly-Cys-PEG2k-LPEI; and wherein said targeting moiety is HOOC(CH$_2$)$_2$—CH(COOH)—NH—CO—NH—CH(COOH)—(CH$_2$)$_2$—CO— (DUPA residue), and wherein said dsRNA is polyinosinic-polycytidylic acid double stranded RNA (poly I:C), and wherein each strand of said dsRNA has 20-300 ribonucleotides.

21. A pharmaceutical composition comprising a pharmaceutically acceptable carrier and a polyplex of claim 1.

22. A pharmaceutical composition comprising a pharmaceutically acceptable carrier and a polyplex of claim 19.

23. A pharmaceutical composition comprising a pharmaceutically acceptable carrier and a polyplex of claim 20.

* * * * *

SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Tyr His Trp Tyr Gly Tyr Thr Pro Gln Asn Val Ile
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: X is 8-aminooctanoic acid.
<222> LOCATION: (1)..(1)

<400> SEQUENCE: 2

Xaa Phe Gly Trp Trp Gly Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: X is 8-aminooctanoic acid
<222> LOCATION: (1)..(1)
<220> FEATURE:
<221> NAME/KEY: X is diaminopropionic acid
<222> LOCATION: (4)..(4)

<400> SEQUENCE: 3

Xaa Phe Phe Xaa Asp Cys
1               5

<210> SEQ ID NO 4
<211> LENGTH: 82
<212> TYPE: PRT
<213> ORGANISM: Artificial Sequence
<220> FEATURE:
<223> OTHER INFORMATION: Synthetic

<400> SEQUENCE: 4

Met Gly Ser Ser His His His His His Ser Ser Gly Leu Val Pro
1               5                   10                  15

Arg Gly Ser His Met Ala Ser Ala Glu Ala Lys Tyr Ala Lys Glu Met
            20                  25                  30

Trp Ala Ala Trp Glu Glu Ile Arg Asn Leu Pro Asn Leu Thr Gly Trp
        35                  40                  45

Gln Met Thr Ala Phe Ile Ala Lys Leu Val Asp Asp Pro Ser Gln Ser
    50                  55                  60

Ser Glu Leu Leu Ser Glu Ala Lys Lys Leu Asn Asp Ser Gln Ala Pro
65                  70                  75                  80

Lys Cys

<210> SEQ ID NO 5
<211> LENGTH: 79
<212> TYPE: PRT
<213> ORGANISM: Artificial Sequence
<220> FEATURE:
<223> OTHER INFORMATION: Synthetic

<400> SEQUENCE: 5

Met Gly Ser Ser His His His His His Ser Ser Gly Leu Val Pro
1               5                   10                  15

Arg Gly Ser His Met Ala Glu Ala Lys Tyr Ala Lys Met Arg Asn Ala
            20                  25                  30

Tyr Trp Glu Ile Ala Leu Leu Pro Asn Leu Thr Asn Gln Gln Lys Arg
        35                  40                  45

Ala Phe Ile Arg Lys Leu Tyr Asp Asp Pro Ser Gln Ser Ser Glu Leu
    50                  55                  60

Leu Ser Glu Ala Lys Lys Leu Asn Asp Ser Gln Ala Pro Lys Cys
65                  70                  75

<210> SEQ ID NO 6
<211> LENGTH: 53
<212> TYPE: PRT
<213> ORGANISM: Homo sapiens

<400> SEQUENCE: 6

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50